US008439954B2

(12) United States Patent
Abdelgany

(10) Patent No.: US 8,439,954 B2
(45) Date of Patent: May 14, 2013

(54) SPRING-LOADED, LOAD SHARING POLYAXIAL PEDICLE SCREW ASSEMBLY AND METHOD

(75) Inventor: Mahmoud F. Abdelgany, Rockaway, NJ (US)

(73) Assignee: Custom Spine, Inc., Parsippany, NJ (US)

( * ) Notice: Subject to any disclaimer, the term of this patent is extended or adjusted under 35 U.S.C. 154(b) by 340 days.

(21) Appl. No.: 13/005,227

(22) Filed: Jan. 12, 2011

(65) Prior Publication Data

US 2011/0112582 A1 May 12, 2011

Related U.S. Application Data

(60) Division of application No. 11/608,857, filed on Dec. 11, 2006, now Pat. No. 7,892,257, which is a continuation-in-part of application No. 11/045,908, filed on Jan. 28, 2005, now Pat. No. 7,862,594.

(60) Provisional application No. 60/548,543, filed on Feb. 27, 2004, provisional application No. 60/565,658, filed on Apr. 27, 2004.

(51) Int. Cl.
*A61B 17/88* (2006.01)
(52) U.S. Cl.
USPC .......................................................... 606/279
(58) Field of Classification Search .................. 606/246, 606/257, 266, 268–270, 290, 294, 300
See application file for complete search history.

(56) References Cited

U.S. PATENT DOCUMENTS

| 3,054,321 | A | 9/1962 | Macchia |
| 4,887,596 | A | 12/1989 | Sherman |
| 4,946,458 | A | 8/1990 | Harms et al. |
| 5,067,955 | A | 11/1991 | Cotrel |
| 5,129,388 | A | 7/1992 | Vignaud et al. |
| 5,246,442 | A | 9/1993 | Ashman et al. |
| 5,360,431 | A | 11/1994 | Puno et al. |
| 5,443,467 | A | 8/1995 | Biedermann et al. |
| 5,466,237 | A | 11/1995 | Byrd, III et al. |
| 5,474,555 | A | 12/1995 | Puno et al. |
| 5,476,464 | A | 12/1995 | Metz-Stavenhagen et al. |
| 5,520,689 | A | 5/1996 | Schlapfer et al. |
| 5,536,268 | A | 7/1996 | Griss |
| 5,545,165 | A | 8/1996 | Biedermann et al. |

(Continued)

FOREIGN PATENT DOCUMENTS

| DE | 19950075 | 4/2001 |
| EP | 1090595 | 4/2001 |

(Continued)

*Primary Examiner* — Kevin T Truong
*Assistant Examiner* — Sameh Boles
(74) *Attorney, Agent, or Firm* — Rahman LLC

(57) ABSTRACT

A method includes positioning a load sharing mechanism in between a screw head and a bone fixator component; attaching the screw head to the bone fixator component such that the load sharing mechanism provides tensile resistance to the screw head; securing the bone fixator component in a bone; securing a locking pin in the screw head; engaging the locking pin with the bone fixator component; inserting a longitudinal member in the screw head; and inserting a blocker in the screw head. The method may further comprise positioning a longitudinal member in a slot configured in the screw head.

19 Claims, 19 Drawing Sheets

U.S. PATENT DOCUMENTS

| | | | |
|---|---|---|---|
| 5,669,911 | A | 9/1997 | Errico et al. |
| 5,672,176 | A | 9/1997 | Biedermann et al. |
| 5,733,286 | A | 3/1998 | Errico et al. |
| 5,735,851 | A | 4/1998 | Errico et al. |
| 5,752,957 | A * | 5/1998 | Ralph et al. ............ 606/266 |
| 5,863,293 | A | 1/1999 | Richelsoph |
| 5,879,350 | A | 3/1999 | Sherman et al. |
| 5,882,350 | A | 3/1999 | Ralph et al. |
| 5,885,286 | A | 3/1999 | Sherman et al. |
| 5,951,553 | A | 9/1999 | Betz et al. |
| 5,964,760 | A | 10/1999 | Richelsoph |
| 5,964,767 | A | 10/1999 | Tapia et al. |
| 5,989,250 | A | 11/1999 | Wagner et al. |
| 6,022,350 | A | 2/2000 | Ganem |
| 6,030,389 | A | 2/2000 | Wagner et al. |
| 6,045,579 | A | 4/2000 | Hochshuler et al. |
| 6,053,917 | A | 4/2000 | Sherman et al. |
| 6,063,090 | A | 5/2000 | Schlapfer |
| 6,074,391 | A | 6/2000 | Metz-Stavenhagen et al. |
| 6,077,262 | A | 6/2000 | Schlapfer et al. |
| 6,090,110 | A | 7/2000 | Metz-Stavenhagen |
| 6,090,111 | A | 7/2000 | Nichols |
| 6,113,601 | A | 9/2000 | Tatar |
| 6,132,430 | A | 10/2000 | Wagner |
| 6,132,432 | A | 10/2000 | Richelsoph |
| 6,187,005 | B1 | 2/2001 | Brace et al. |
| 6,248,105 | B1 | 6/2001 | Schlapfer et al. |
| 6,273,888 | B1 | 8/2001 | Justis |
| 6,280,442 | B1 | 8/2001 | Barker et al. |
| 6,290,703 | B1 | 9/2001 | Ganem |
| 6,302,888 | B1 | 10/2001 | Mellinger et al. |
| RE37,665 | E | 4/2002 | Ralph et al. |
| 6,368,321 | B1 | 4/2002 | Jackson |
| 6,371,957 | B1 | 4/2002 | Amrein et al. |
| 6,416,515 | B1 | 7/2002 | Wagner |
| 6,454,769 | B2 | 9/2002 | Wagner et al. |
| 6,475,218 | B2 | 11/2002 | Gournay et al. |
| 6,485,491 | B1 | 11/2002 | Farris et al. |
| 6,485,492 | B1 | 11/2002 | Halm et al. |
| 6,488,681 | B2 | 12/2002 | Martin et al. |
| 6,554,834 | B1 | 4/2003 | Crozet et al. |
| 6,562,040 | B1 | 5/2003 | Wagner |
| 6,565,565 | B1 | 5/2003 | Yuan et al. |
| 6,595,992 | B1 | 7/2003 | Wagner et al. |
| 6,610,063 | B2 | 8/2003 | Kumar et al. |
| 6,613,050 | B1 | 9/2003 | Wagner et al. |
| 6,623,485 | B2 | 9/2003 | Doubler et al. |
| 6,626,908 | B2 | 9/2003 | Cooper et al. |
| 6,641,586 | B2 | 11/2003 | Varieur |
| 6,648,888 | B1 | 11/2003 | Shluzas |
| 6,660,004 | B2 | 12/2003 | Barker et al. |
| 6,736,820 | B2 | 5/2004 | Biedermann et al. |
| 6,780,186 | B2 | 8/2004 | Errico et al. |
| 6,858,030 | B2 | 2/2005 | Martin et al. |
| 6,881,215 | B2 | 4/2005 | Assaker et al. |
| 6,890,334 | B2 | 5/2005 | Brace et al. |
| 6,896,677 | B1 | 5/2005 | Lin |
| 6,974,460 | B2 | 12/2005 | Carbone et al. |
| 7,022,122 | B2 | 4/2006 | Amrein et al. |
| RE39,089 | E | 5/2006 | Ralph et al. |
| 7,118,571 | B2 | 10/2006 | Kumar et al. |
| 7,128,743 | B2 | 10/2006 | Metz-Stavenhagen |
| 7,524,326 | B2 | 4/2009 | Dierks |
| 2002/0010467 | A1 | 1/2002 | Cooper et al. |
| 2003/0055426 | A1 | 3/2003 | Carbone et al. |
| 2003/0073996 | A1 | 4/2003 | Doubler et al. |
| 2003/0163133 | A1 | 8/2003 | Altarac et al. |
| 2003/0199873 | A1 | 10/2003 | Richelsoph |
| 2004/0153077 | A1 | 8/2004 | Biedermann et al. |
| 2005/0113927 | A1 | 5/2005 | Malek |
| 2006/0241599 | A1 | 10/2006 | Konieczynski et al. |

FOREIGN PATENT DOCUMENTS

| | | |
|---|---|---|
| EP | 1254640 | 11/2002 |
| EP | 1293168 | 3/2003 |
| WO | 9834554 | 8/1998 |
| WO | 9955246 | 11/1999 |
| WO | 0122893 | 4/2001 |
| WO | 03068088 | 8/2003 |

* cited by examiner

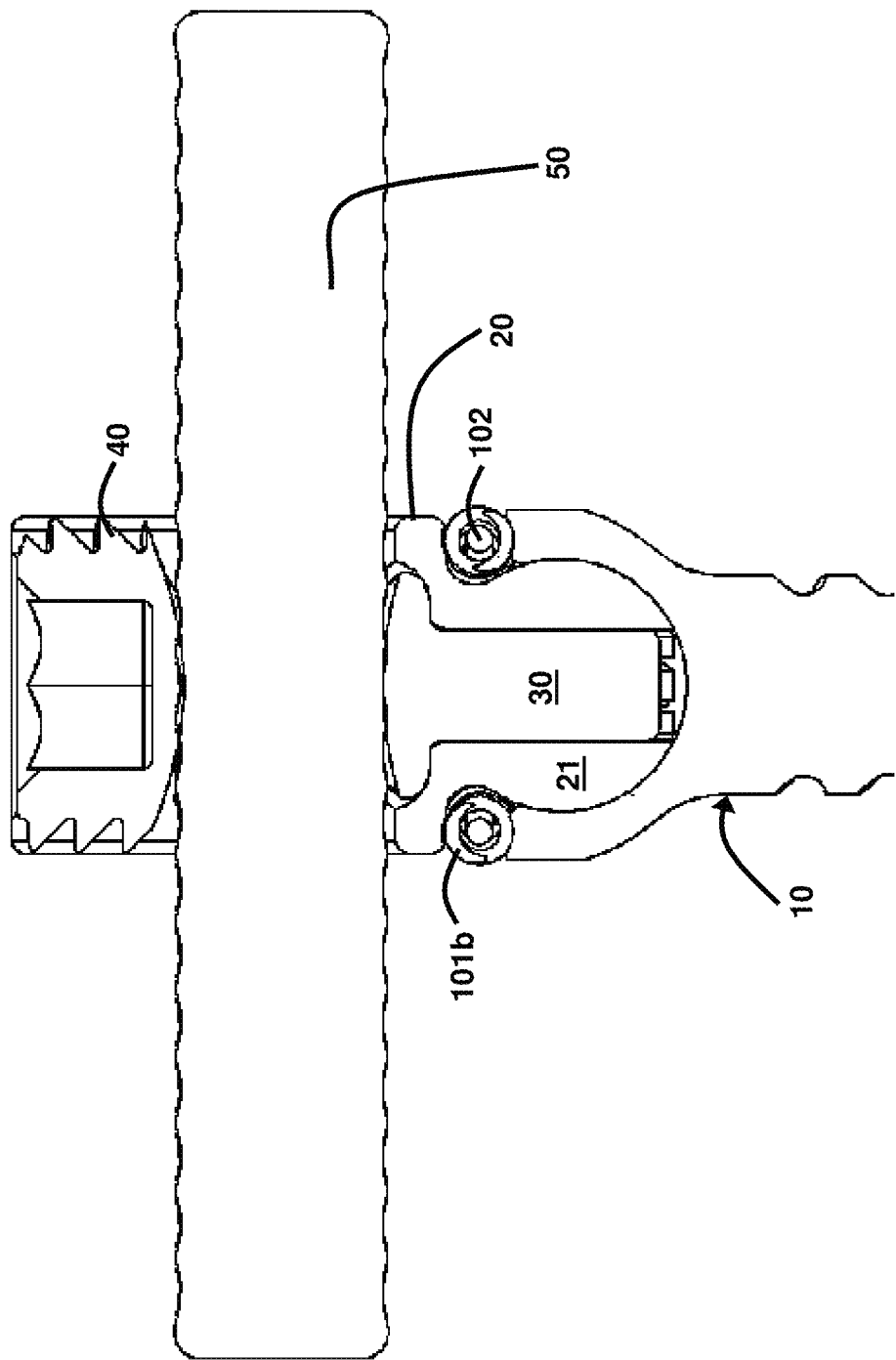

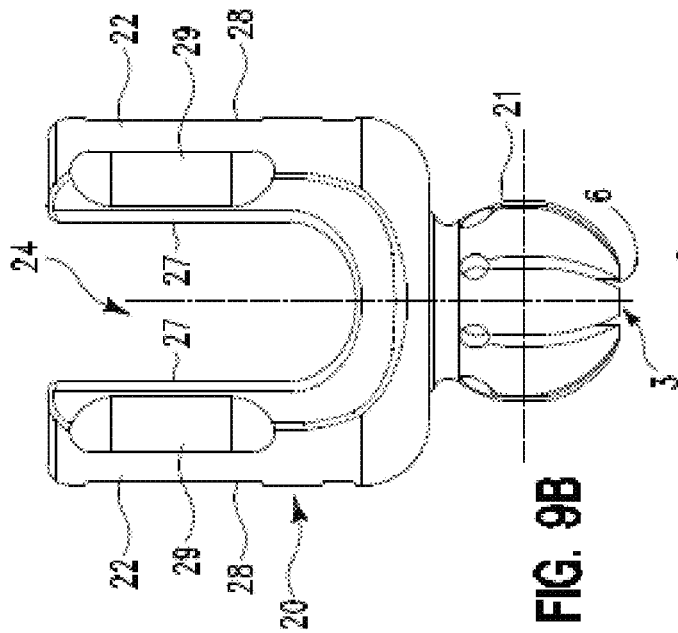
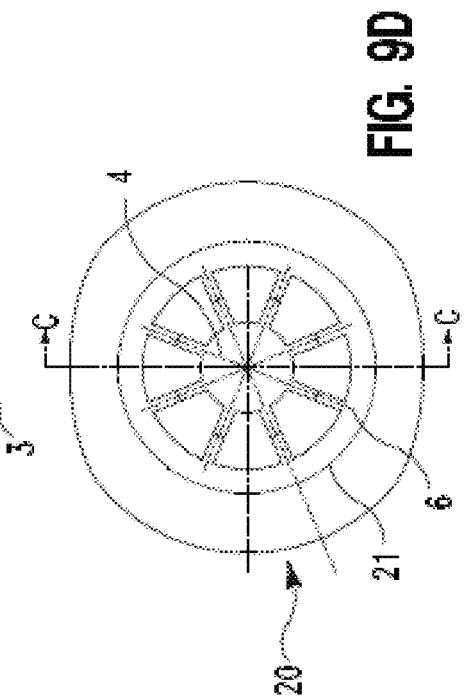
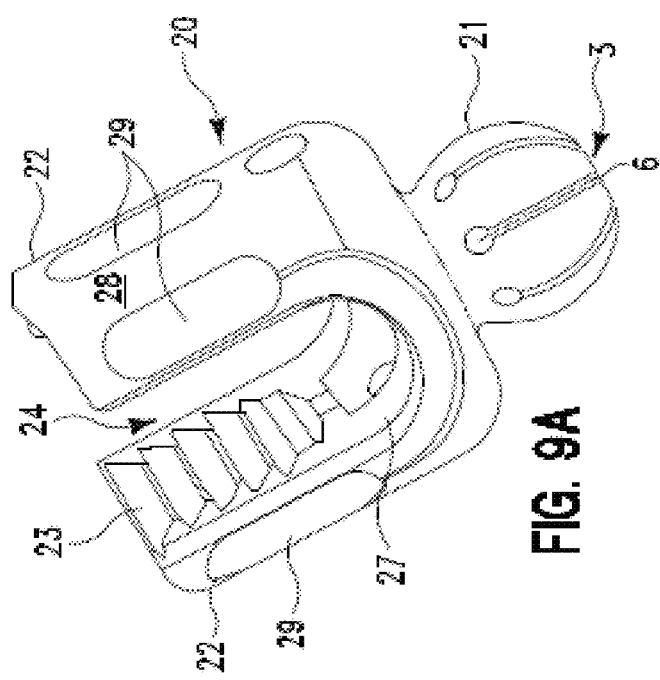
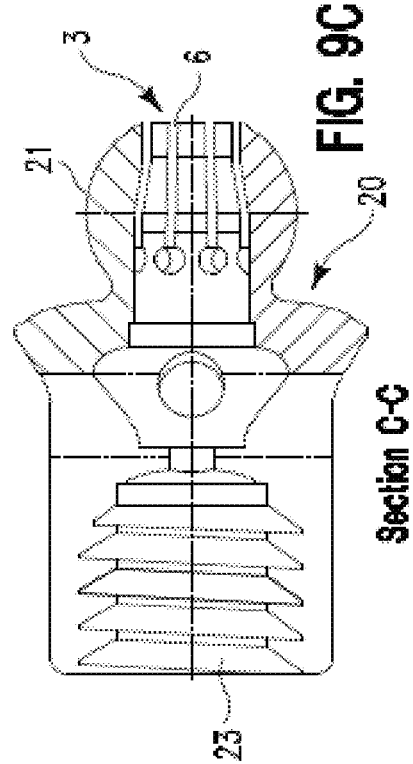

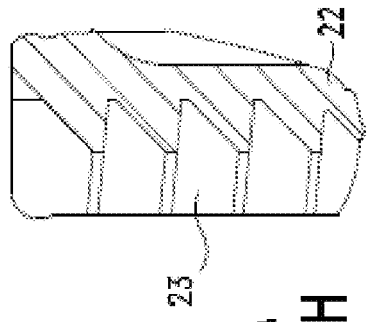
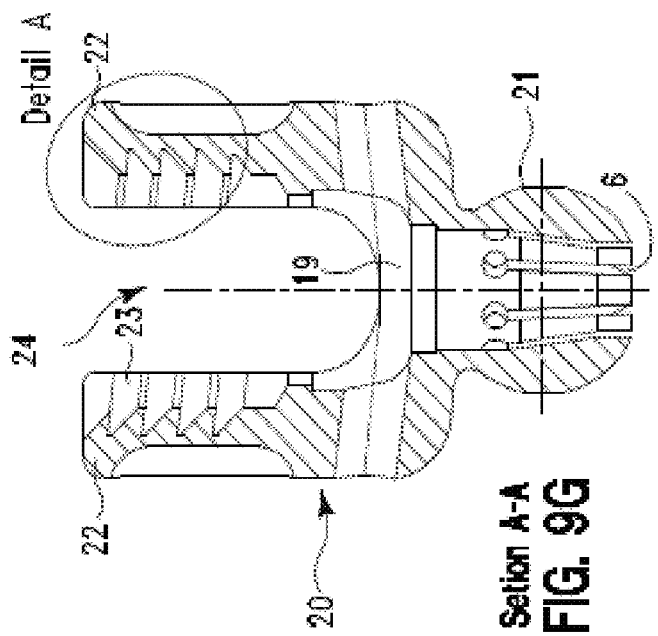
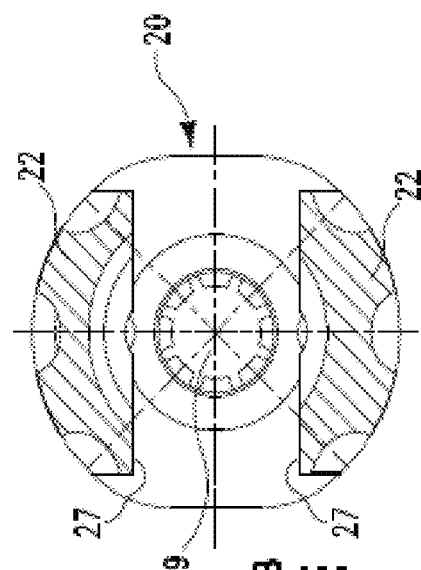
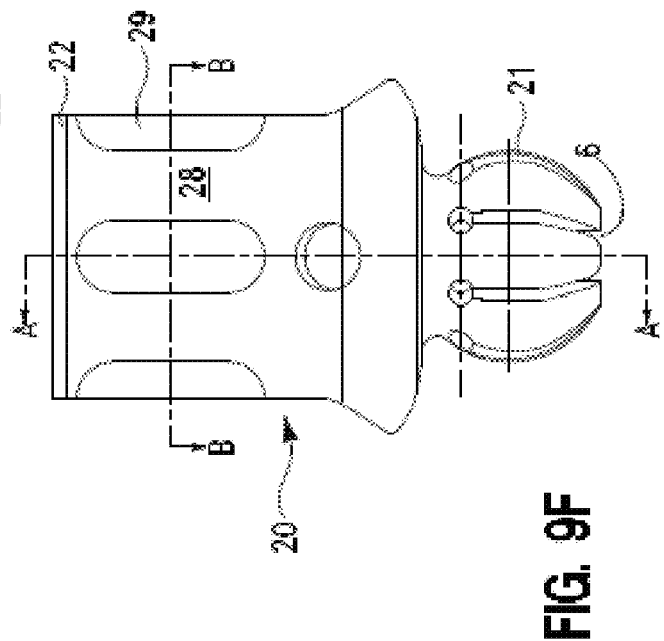

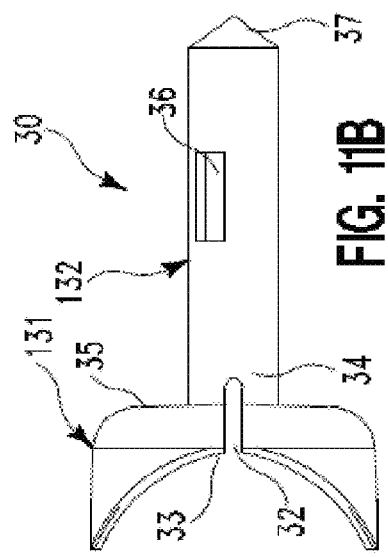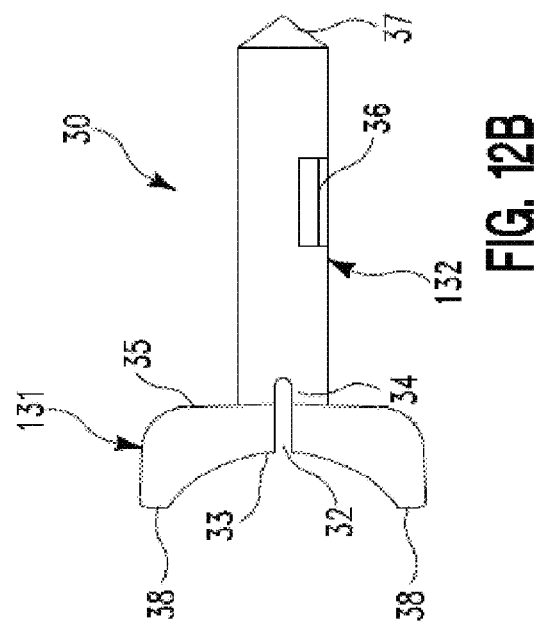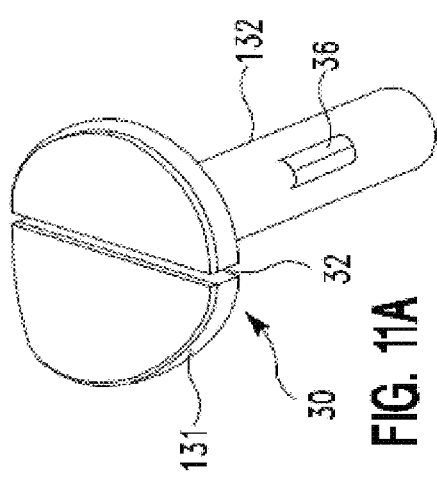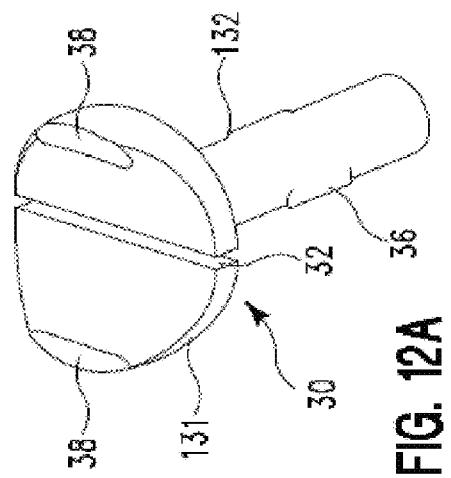

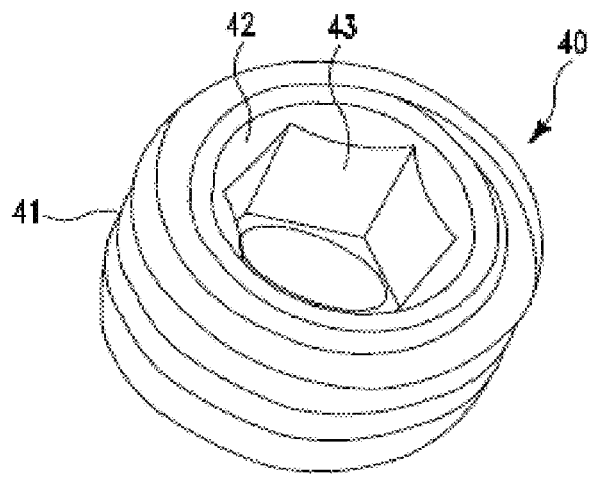
FIG. 15A
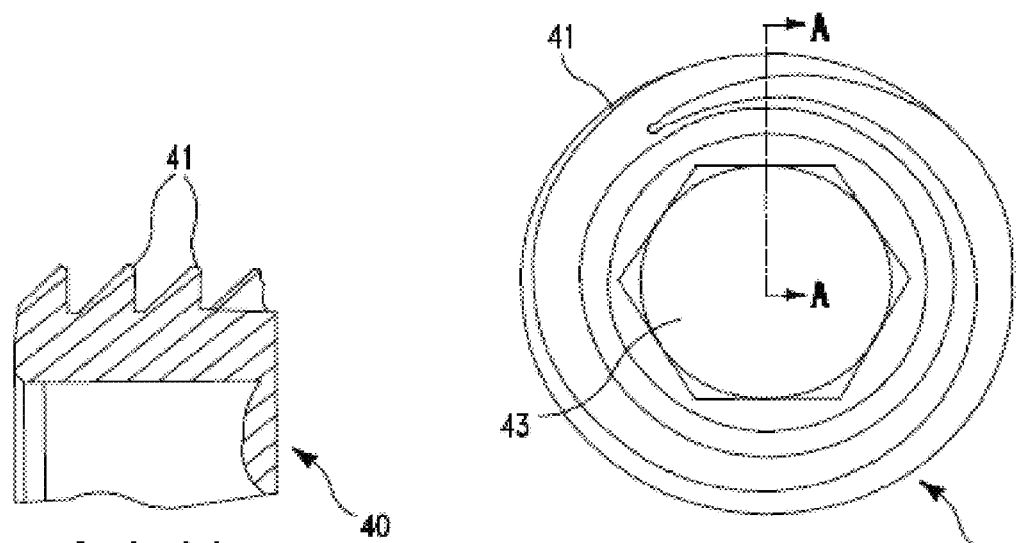
Section A-A
FIG. 15C
FIG. 15B

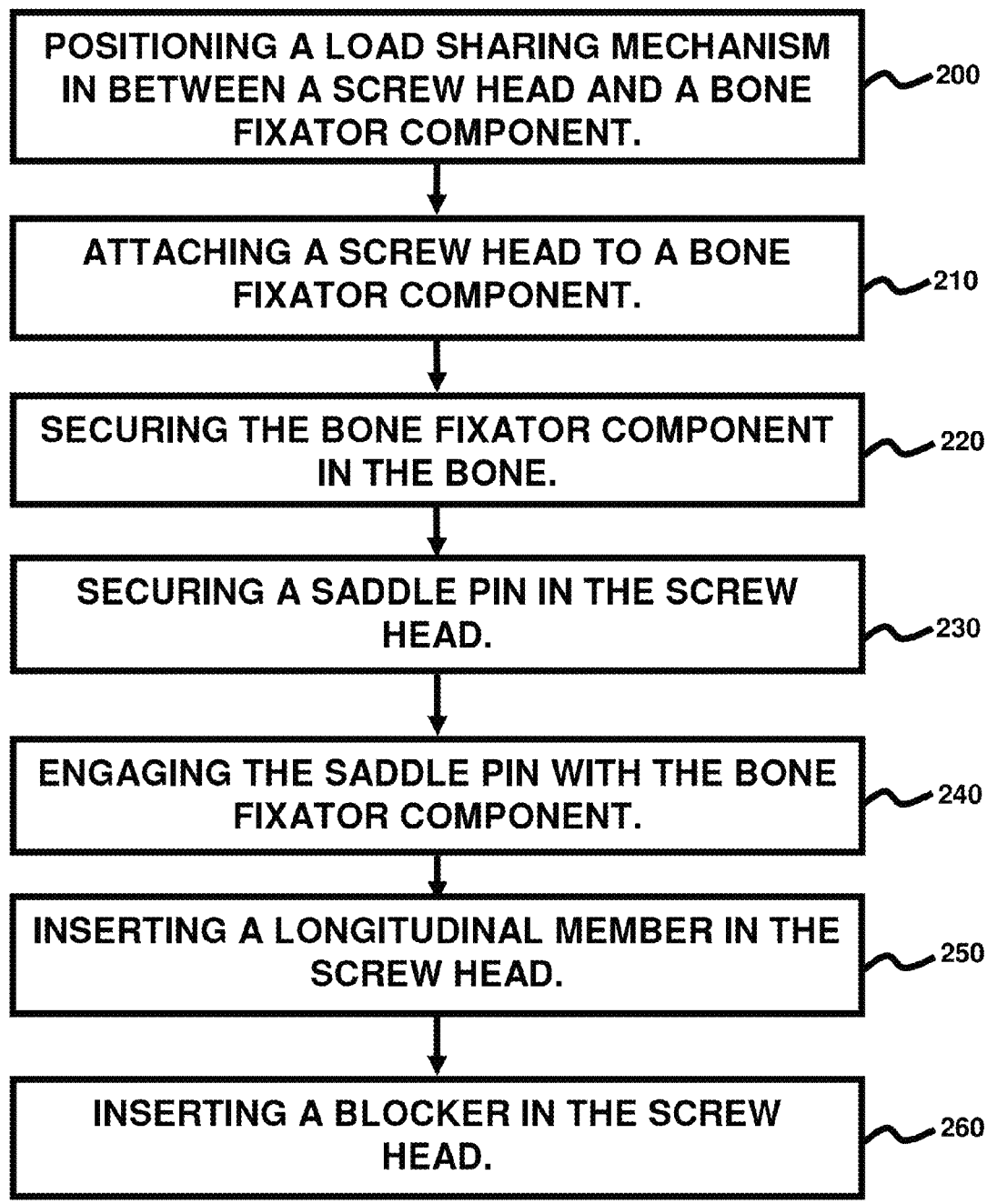

SPRING-LOADED, LOAD SHARING POLYAXIAL PEDICLE SCREW ASSEMBLY AND METHOD

CROSS REFERENCE TO RELATED APPLICATION

This application is a divisional of U.S. patent application Ser. No. 11/608,857 filed on Dec. 11, 2006, which is a continuation-in-part (CIP) of U.S. patent application Ser. No. 11/045,908 filed on Jan. 28, 2005 and entitled "Polyaxial Pedicle Screw Assembly" and now U.S. Pat. No. 7,862,594 issued on Jan. 4, 2011, which claims the benefit of U.S. Provisional Patent Application No. 60/548,543 filed on Feb. 27, 2004 and entitled "Polyaxial Pedicle Screw Assembly" and U.S. Provisional Patent Application No. 60/565,658 filed on Apr. 27, 2004 and entitled "Polyaxial Pedicle Screw Assembly," the complete disclosures of which, in their entireties, are herein incorporated by reference.

BACKGROUND

1. Technical Field

The embodiments herein generally relate to medical devices and assemblies, and more particularly to an orthopedic surgical implant assembly used in the field of surgical lumbar, thoracic and cervical spine treatment.

2. Description of the Related Art

Surgical procedures treating spinal injuries are one of the most complex and challenging surgeries for both the patient and the surgeon. When there are various deformities, trauma, or fractures of the vertebra, surgeons may attempt to "fuse" them together by attaching screw-like devices into the pedicles of the spine and thereby connecting several vertebrae (typically two or more) using a semi-rigid rod. However, due to the complexity of the human anatomy, most surgeons must bend the rod (causing notches thereby reducing fatigue resistance) before placing them into two or more non-aligned pedicle screws in order to properly stabilize the pedicle screw assembly within the patient's body.

Additionally, most conventional top loading pedicle screws do not allow for a screw head to be tensioned in a given zone or range of angulations from the fixed bone anchor (i.e., bone screw). Consequentially, most conventional solutions use the rod portion of the system to provide the dynamism. Generally, most artificial discs currently being marketed do not typically offer any resistance at the extreme ranges of motion, and others tend to offer a "dead stop" that may cause implant failure or implant dislodging. As such, most surgeons would concede that the removal of a failed artificial disc is an extremely undesirable event that is laced with major complications. Thus, there remains a need for a new and improved pedicle screw assembly that allows the screw head to be tensioned in a given zone or range of angulations from the fixed bone anchor.

SUMMARY

In view of the foregoing, an embodiment herein provides a method of assembling a pedicle fixation assembly, wherein the method comprises positioning a load sharing mechanism in between a screw head and a bone fixator component; attaching the screw head to the bone fixator component such that the load sharing mechanism provides tensile resistance to the screw head; securing the bone fixator component in a bone; securing a locking pin in the screw head; engaging the locking pin with the bone fixator component; inserting a longitudinal member in the screw head; and inserting a blocker in the screw head. The method may further comprise positioning a longitudinal member in a slot configured in the screw head.

Moreover, the method may further comprise configuring the fixator component with a concave socket that is configured for receiving the bulbous end of the screw head. Additionally, the method may further comprise configuring the load sharing mechanism as any of a wave washer, a collapsible hollow washer, a coiled spring, and a flexible washer. Also, the method may further comprise configuring the load sharing mechanism as a washer having an outer surface with a plurality of cutout portions configured therein. Furthermore, the method may further comprise configuring the fixator component as a bone screw. Moreover, the method may further comprise configuring the fixator component as a hook.

Another embodiment provides a method comprising connecting a bone fixator component to a vertebral body, wherein the bone fixator component comprises an open concave head; providing a screw head comprising: a bulbous body comprising a plurality of outwardly expandable legs adapted to lock into the open concave head of the bone fixator component, wherein the bulbous body comprises a dynamic diameter and the dynamic diameter is between a first diameter and a second diameter; and an upper portion permanently coupled to the bulbous body and comprising a fixed width, wherein the fixed width is greater than the first diameter. The method further includes positioning a load sharing mechanism in between the bone fixator component and the screw head, the load sharing mechanism comprising: an inner load sharing mechanism diameter; and an outer load sharing mechanism diameter, wherein the inner load sharing mechanism diameter is less than the outer load sharing mechanism diameter. The method further includes mounting a pin in the screw head causing expansion of the bulbous body from the first diameter to the second diameter; and engaging a blocker with the screw head.

The load sharing mechanism may comprise any of a wave washer, a collapsible hollow washer, and a flexible washer. The load sharing mechanism may comprise a spring mechanism comprising a coiled spring wrapped in a first spring diameter and an interior rounded washer within the coiled spring. The load sharing mechanism may comprise a washer comprising a top surface; a bottom surface; and a side surface with a plurality of cutout portions configured therein, wherein the plurality of cutout portions are parallel to the top surface and the bottom surface.

The load sharing mechanism may comprise a flexible polymer washer. The screw head may further comprise a slot adapted to receive a longitudinal member; and a plurality of opposed upright ends separated by the slot, wherein each of the opposed upright ends comprise an inner wall and an outer wall, wherein any of the inner wall and the outer wall comprises wall threads, and wherein any of the inner wall and the outer wall comprises grooves. The bulbous body may further comprise a plurality of flanges and an inner portion, wherein the inner portion comprises a channel bored through the bulbous body, and wherein the pin is mounted within an inner portion of the screw head causing outward expansion of the legs of the bulbous body.

Another embodiment provides a method comprising providing a screw head comprising: an outwardly protruding and expandable bulbous end comprising a plurality of flanges and an inner portion, wherein the inner portion comprises a channel bored through the bulbous end; a slot adapted to receive a longitudinal member; and a pair of opposed upright ends separated by the slot, wherein each of the opposed upright ends comprises an inner wall and an outer wall, wherein the inner wall comprises wall threads, and wherein the outer wall comprises grooves; configuring a fixator component to receive the bulbous end of the screw head; positioning a load sharing mechanism in between the bulbous end of the screw head and the fixator component, wherein the load sharing mechanism provides tensile resistance to the screw head; mounting a pin within an inner portion of the screw head causing the flanges of the bulbous end to expand, wherein the pin sits in the channel; and engaging a blocker with the screw head, wherein the blocker comprises blocker threads that mate with the wall threads.

The screw head may comprise an open "U" shaped inner portion comprising the slot and the plurality of opposed upright ends. The fixator component may comprise a concave socket configured for receiving the bulbous end of the screw head. The load sharing mechanism may comprise any of a wave washer, a collapsible hollow washer, a coiled spring, and a flexible washer. The load sharing mechanism may comprise a washer having an outer surface with a plurality of cutout portions configured therein. The fixator component may comprise any of a bone screw and a hook.

The embodiments herein provide a pedicle screw assembly implant device, which may be used anteriorly or posteriorly, and which is capable of being utilized in surgeries to achieve anterior lumbar interbody fusion, posterior lumbar interbody fusion, transverse lumbar interbody fusion, correct degenerative disc disease, adult and pediatric scoliosis as a fixation device, and posterior cervical fusion.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIG. 8(B) is a cross-sectional view of the screw head and bone screw interface of FIG. 8(A) with an interior rounded washer according to the second embodiment herein;

FIGS. 9(A) through 9(H) are isolated views of the screw head according to the embodiments herein;

FIGS. 11(A) through 11(B) are detailed views of the saddle pin according to the embodiments herein;

FIGS. 12(A) through 12(B) are detailed views of alternate configurations of the saddle pin according to the embodiments herein;

FIGS. 15(A) through 15(C) are detailed views of the blocker according to the embodiments herein; and FIG. 16 is a flow diagram illustrating a preferred method according to the embodiments herein.

DETAILED DESCRIPTION OF PREFERRED EMBODIMENTS

Figure 1:
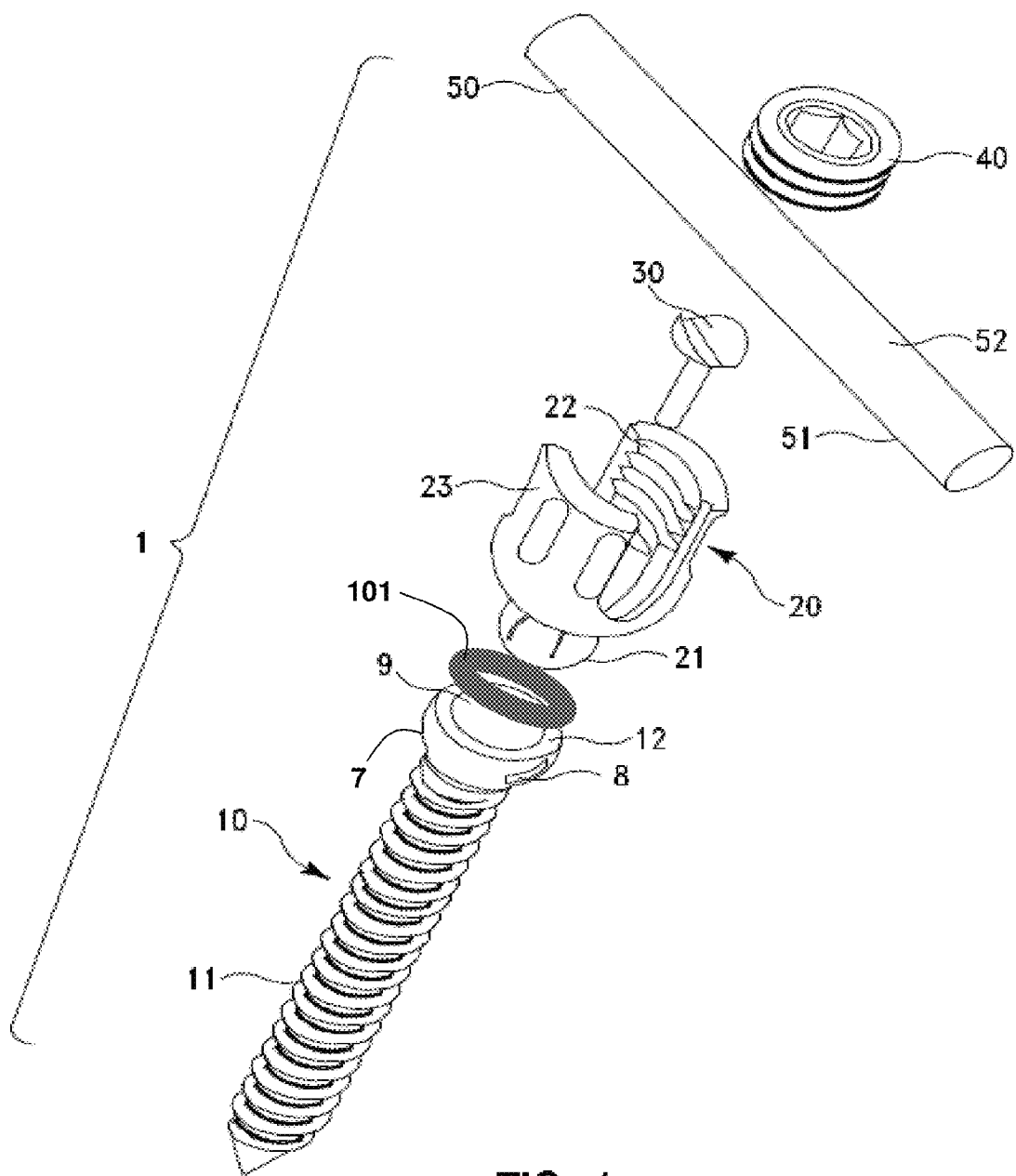
FIG. 1 illustrates an exploded view of the screw assembly according to the embodiments herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned, there remains a need for a new and improved pedicle screw assembly that allows the screw head to be tensioned in a given zone or range of angulations from the fixed bone anchor. The embodiments herein address this need by providing an improved polyaxial pedicle screw device and method of assembly that includes a load sharing mechanism, preferably embodied as a washer, that is capable of allowing the screw head to be tensioned in a given zone or range of angulations from the fixed bone anchor. Referring now to the drawings and more particularly to FIGS. 1 through 16 where similar reference characters denote corresponding features consistently throughout the figures, there are shown preferred embodiments.

FIGS. 1 through 5 provide an exploded view of the pedicle screw assembly 1 according to the embodiments herein. The screw assembly 1 comprises a bone screw (fixator component) 10 having a threaded end 11 for engaging a bone (not shown) and a concave female socket end 12 for engaging and receiving the screw head 20. Additionally, a load sharing mechanism 101 is included between the bone screw 10 and the screw head 20.

Due to the unique nature of the inverted screw design of the assembly 1, the embodiments herein offer excellent geometry to provide long lasting limited yet tensioned range of angulations of the screw head 20 relative to the bone screw 10. By eliminating or minimizing the expansion effect on the spherical portion 21 of the screw head 20 by the saddle pin 30, or by possibly utilizing ceramic coating on the mating concave female socket end 12 of the bone screw 10 and spherical portion 21 of the screw head 20, and installing the load sharing mechanism 101, which may be embodied as a spring mechanism between the bone screw 10 and screw head 20, one can achieve a dynamic stabilization assembly 1 using simple solid fatigue resistant longitudinal members 50.

The motion is limited by the space between the screw head 20 and the top (concave female socket end 12) of the bone screw 10 along with the load sharing mechanism 101. As the human spine attempts higher ranges of motion (causing pain and instability), the embodiments herein offer increased resistance, possibly acting as an artificial muscle. The assembly 1 has many uses and may be used in various configurations of fixed, polyaxial, and dynamic screw systems including: a micro-motion fusion adjunct system that provides load sharing and helps avoid adjacent disc disease; a facet replacement system by providing torsional, axial, flexion, and extension ranges of motion; a load sharing and motion limiting system to complement a discectomy and postpone a fusion for several years; and a load sharing and motion limiting system to complement many of the conventional artificial discs currently being marketed and possibly being marketed in the future.

Figure 2:
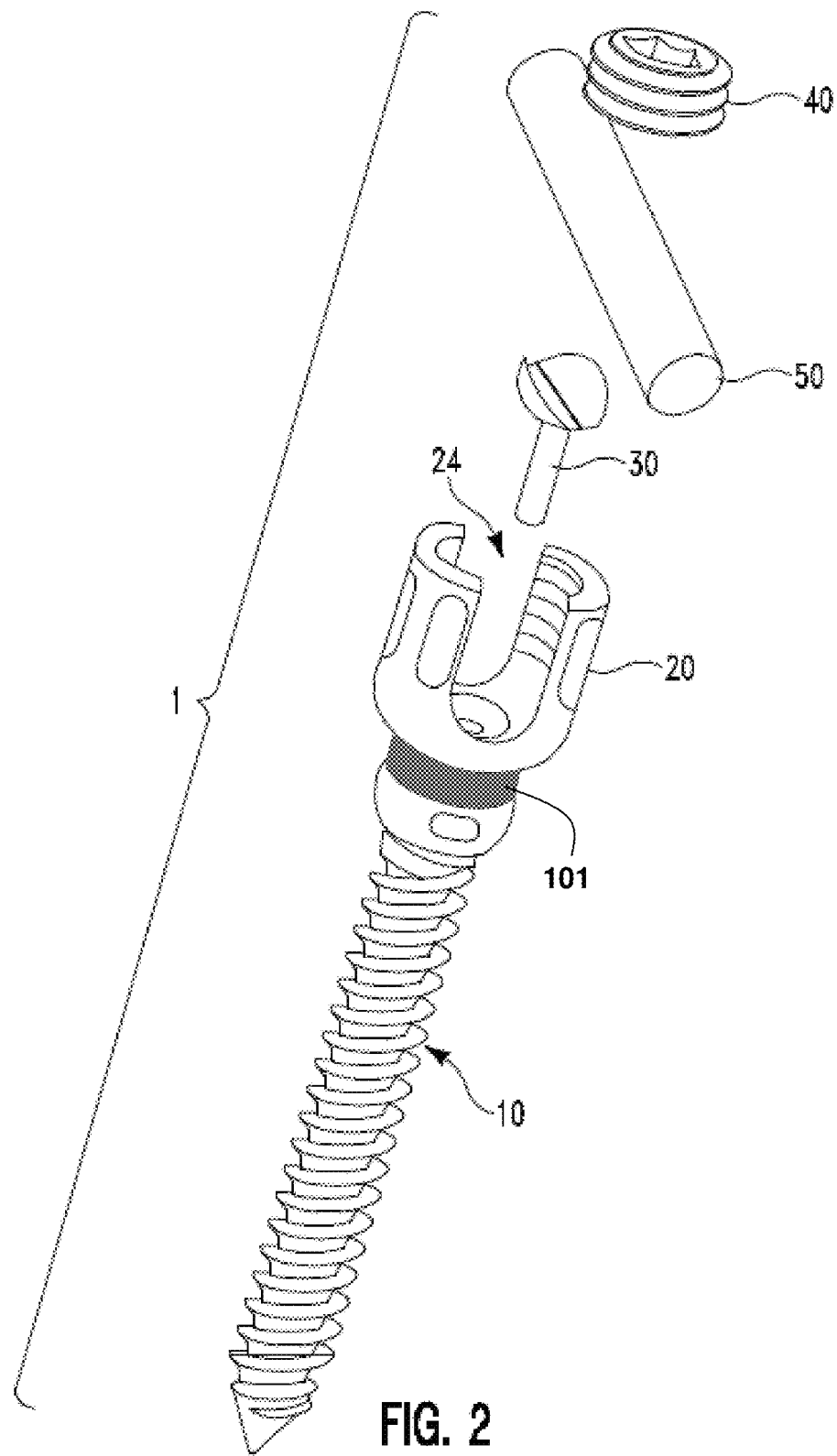
FIG. 2 illustrates an exploded view of the screw assembly during a step in the manufacturing according to the embodiments herein.
Figure 3:
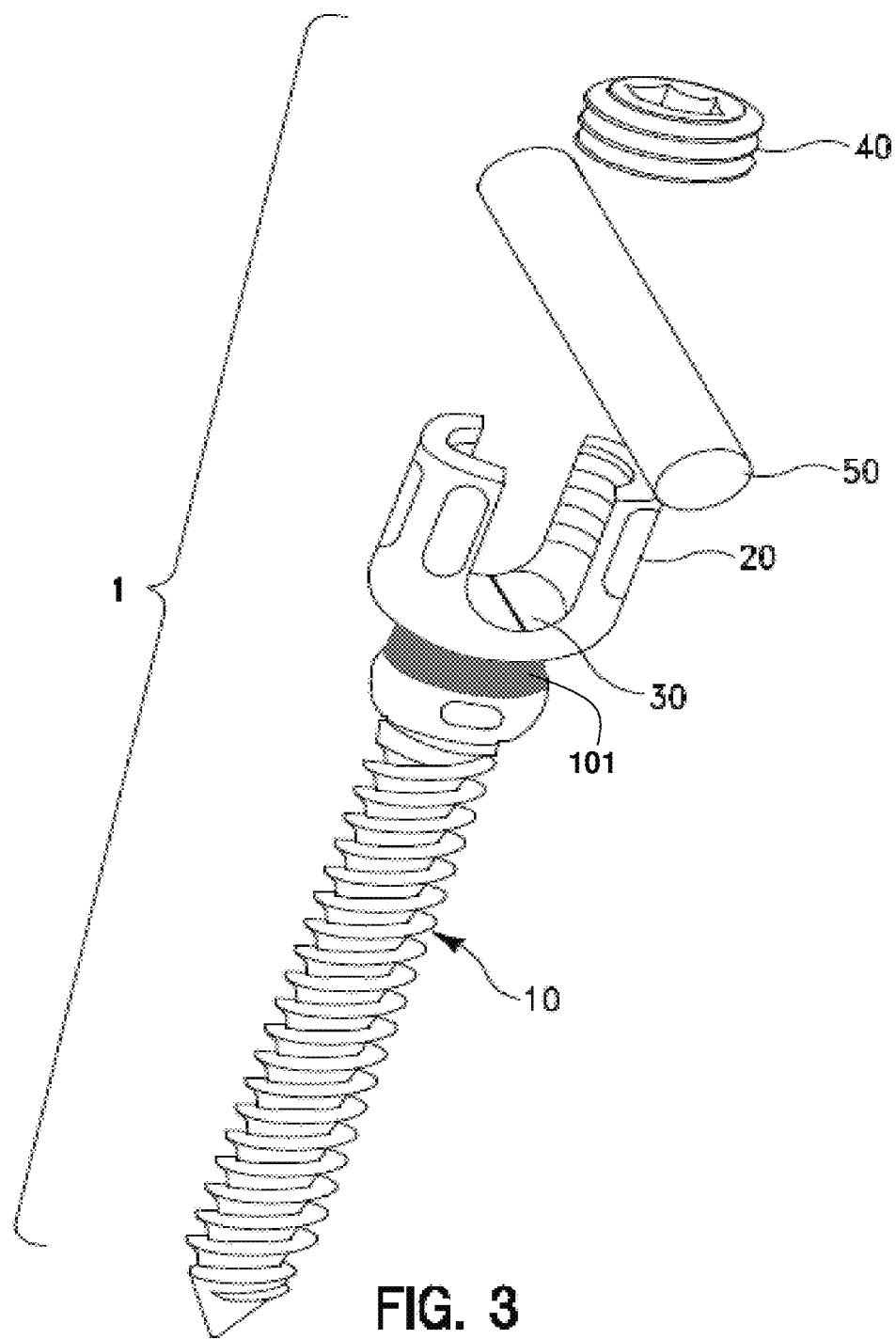
FIG. 3 illustrates an exploded view of the screw assembly during a step in the manufacturing according to the embodiments herein.

As implemented, the load sharing mechanism 101 is placed between the bone screw 10 and the screw head 20 and then the screw head 20 is first snapped into place in the bone screw 10 as shown in FIG. 2. Then, as shown in FIG. 3 the saddle pin 30 snaps into place in the lower base portion 25 of the screw head 20, which includes a groove 26 (best seen in FIG. 7) for receiving the saddle pin 30. In the manufacturing process, once the saddle pin 30 snaps into place, the screw assembly 1 is prepared for ultra sonic cleaning to remove any impurities and subsequently may be shipped in this manufactured format (with the saddle pin 30 connected to the screw head 20, which is connected to the bone screw 10).

The female spherical pocket 12 of the bone screw 10 has an undercut 7 to allow the screw head 20 to pivot freely but not to disassemble once the expanding saddle pin 30 is inserted. The thread 11 of the bone screw 10 may be a multiple lead thread to allow faster insertion into a bone. This thread 11 may be tapered on the minor diameter while cylindrical on the major diameter to allow a new "bite" with every turn and to accommodate more thread depth towards the bottom of the bone screw 10 for the cancellous bone.

Figure 4:
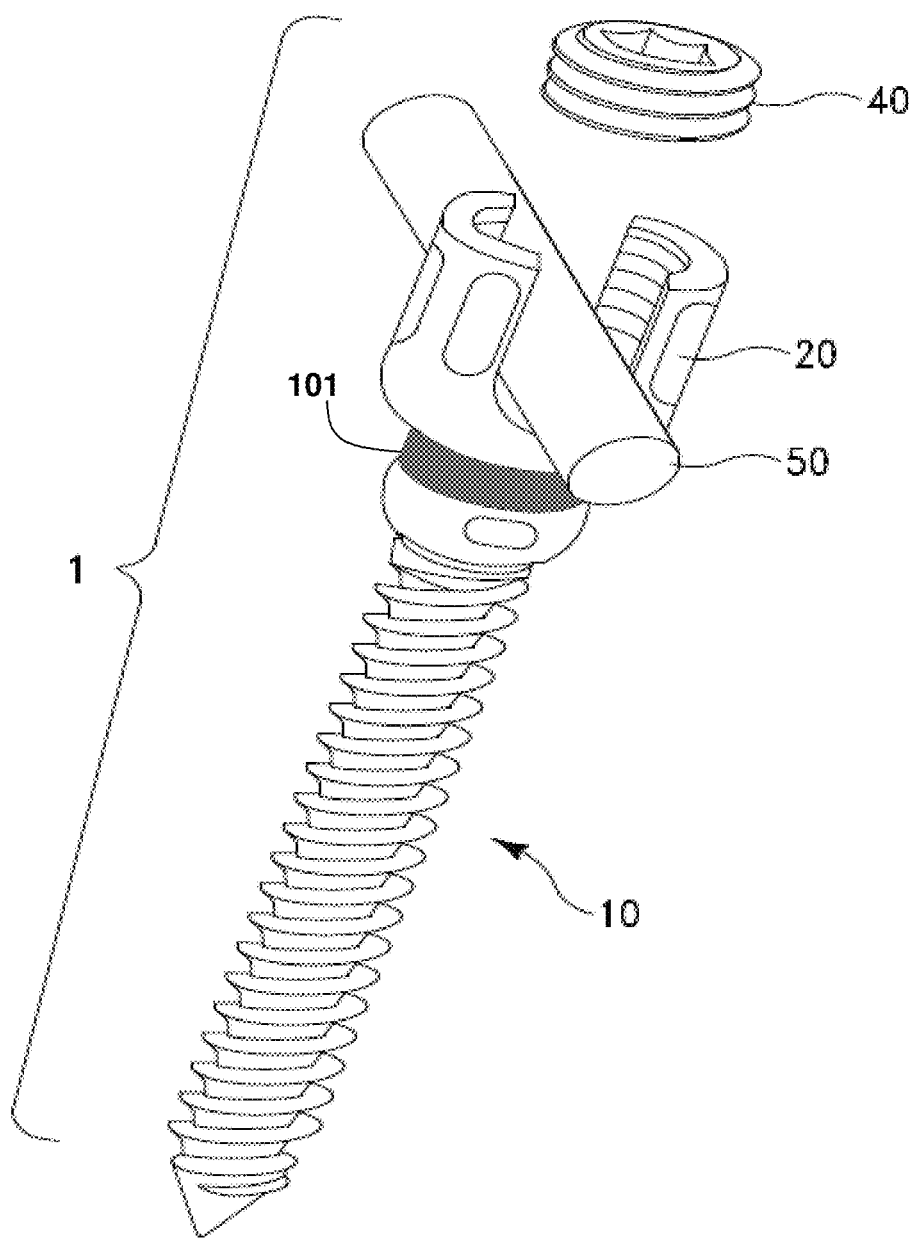
FIG. 4 illustrates an exploded view of the screw assembly during a step in the manufacturing according to the embodiments herein.
Figure 5:
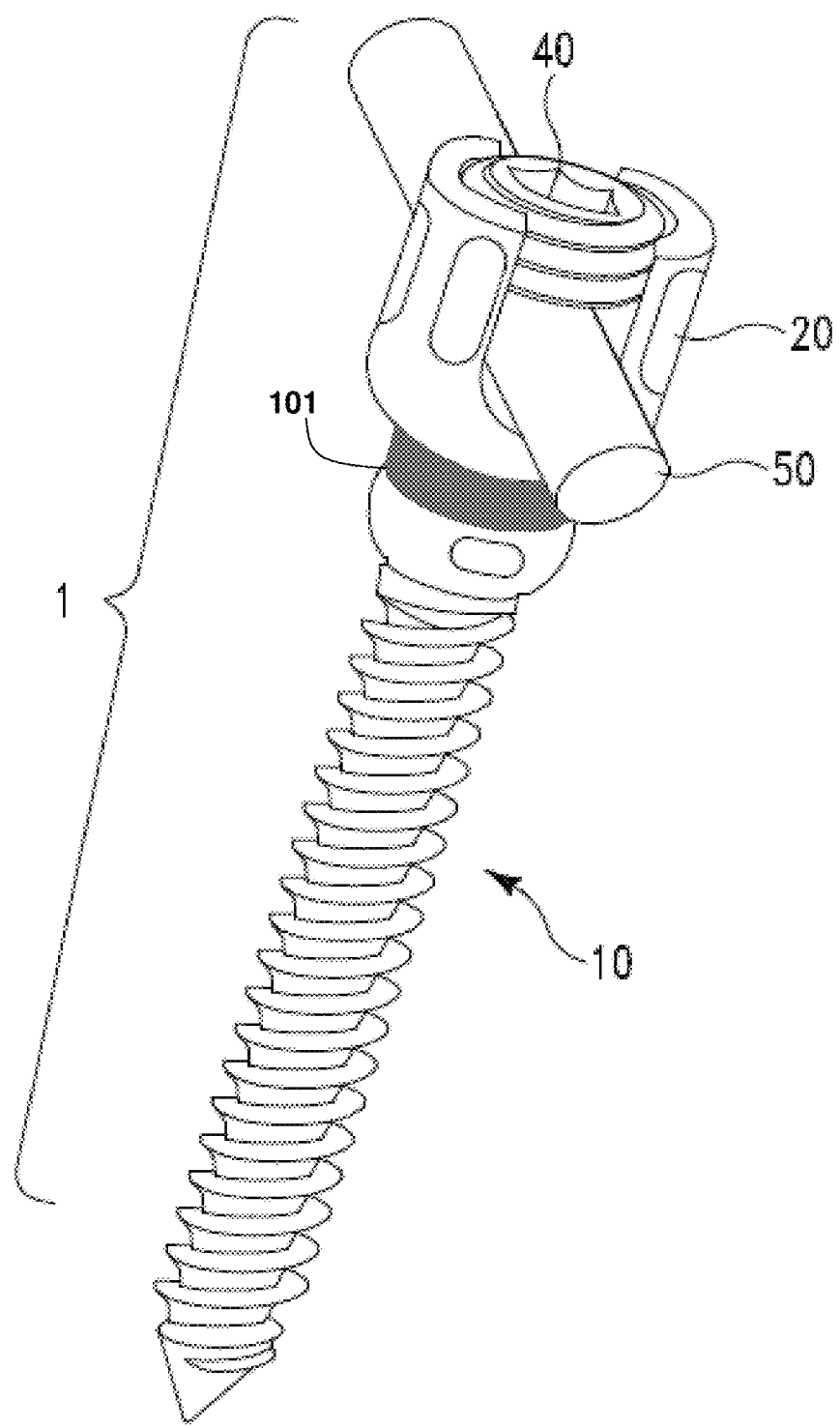
FIG. 5 illustrates a perspective view of the fully assembled screw assembly in a vertical position according to the embodiments herein.

Once the bone screw 10 is inserted into the bone, a longitudinal member 50, which may be embodied as a rod, bar, etc. and blocker 40 are inserted into the screw assembly 1, as illustrated in FIG. 4. The screw head 20 can accommodate 5.5 mm as well as 6.0 mm rods, which is advantageous over conventional screw assemblies that are limited to accepting only rods of a uniform dimension. FIG. 5 illustrates the assembled view of the screw assembly 1 in the straight vertical direction. The threads 11 of the bone screw 10 are double lead, which provides greater surface contact with the bone, but drives at 4 mm/revolution. The screw assembly 1 can also be configured in a rotationally articulated position. The maximum angulation is 25 degrees/side, but the medial correction/travel of the longitudinal member 50 is 3.2 mm/side, which is nearly twice of what most conventional screws offer.

Figure 6A:
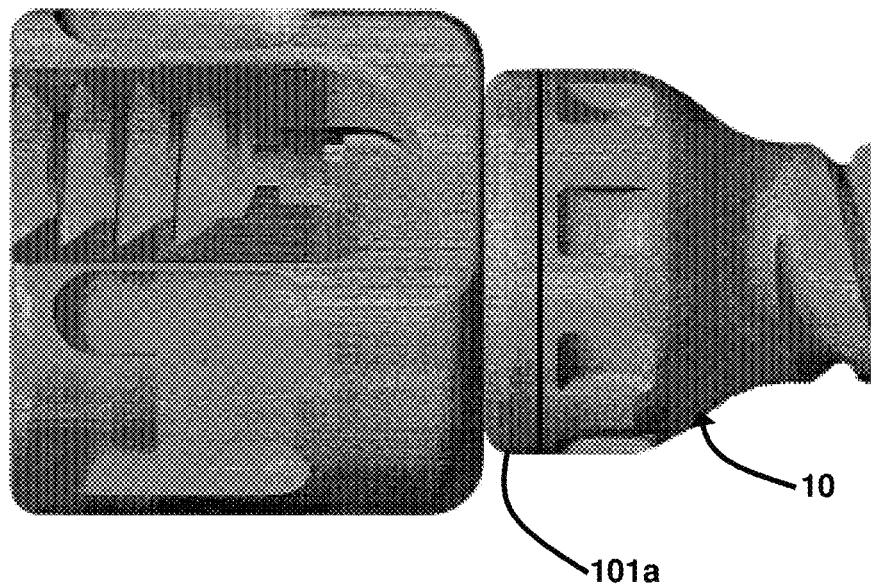
FIG. 6(A) illustrates an isolated perspective view of the screw head and bone screw interface according to a first embodiment herein.
Figure 6B:
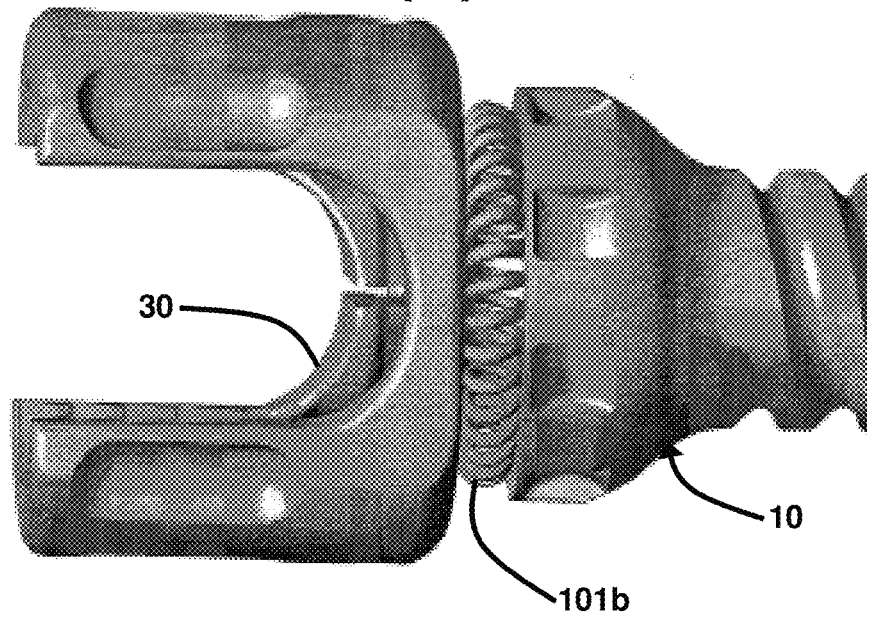
FIG. 6(B) illustrates an isolated perspective view of the screw head and bone screw interface according to a second embodiment herein.
Figure 7A:
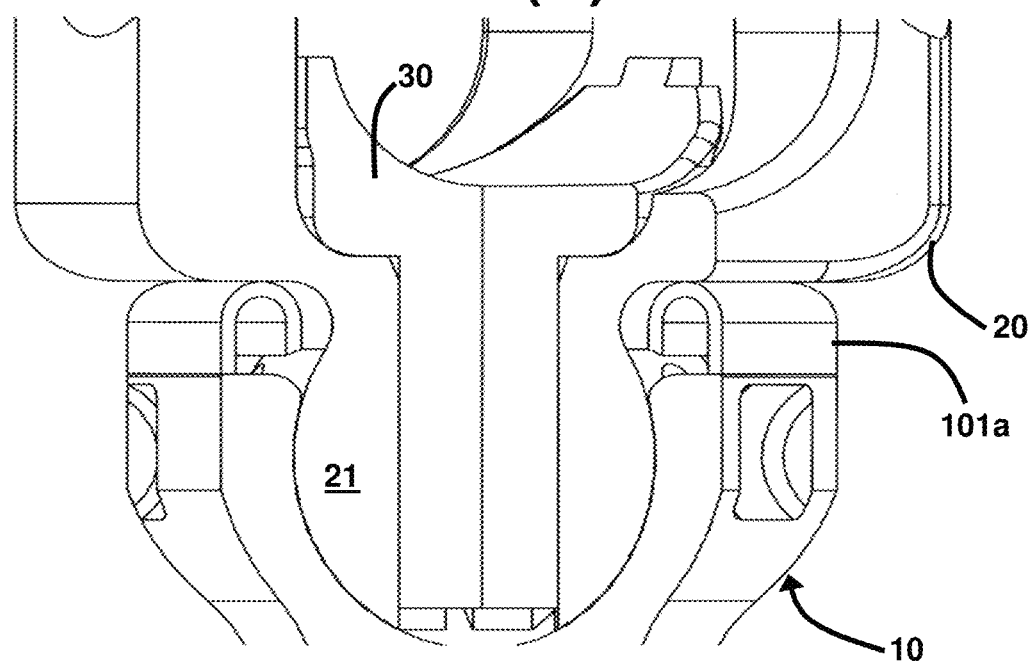
FIG. 7(A) is a cross-sectional view of the screw head and bone screw interface of FIG. 6(A) according to the first embodiment herein.
Figure 7B:
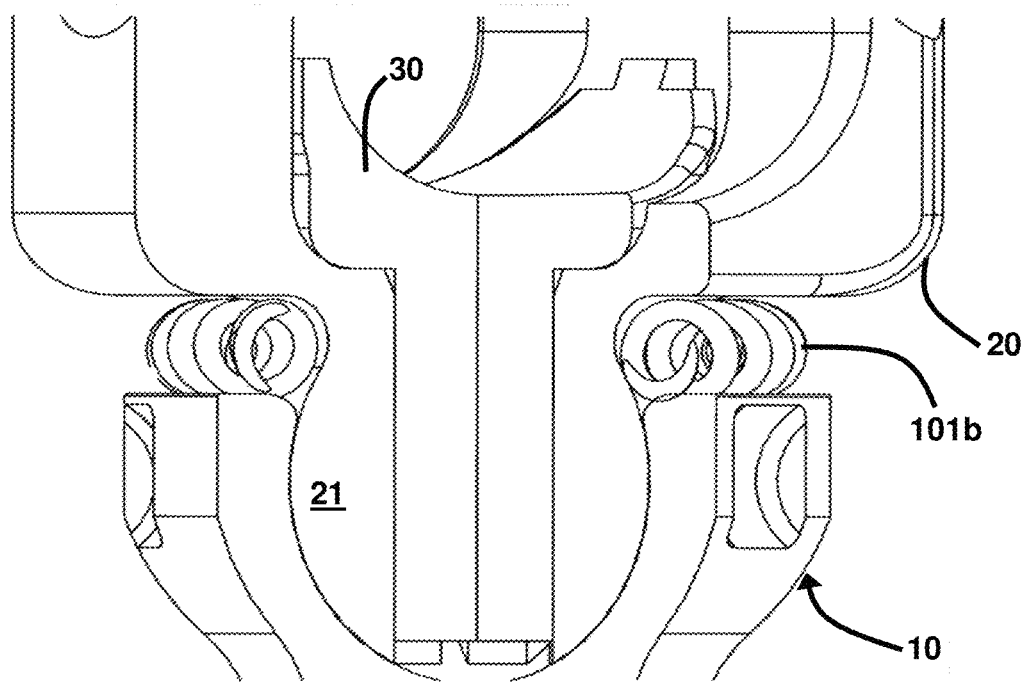
FIG. 7(B) is a cross-sectional view of the screw head and bone screw interface of FIG. 6(B) according to the second embodiment herein.
Figure 8A:
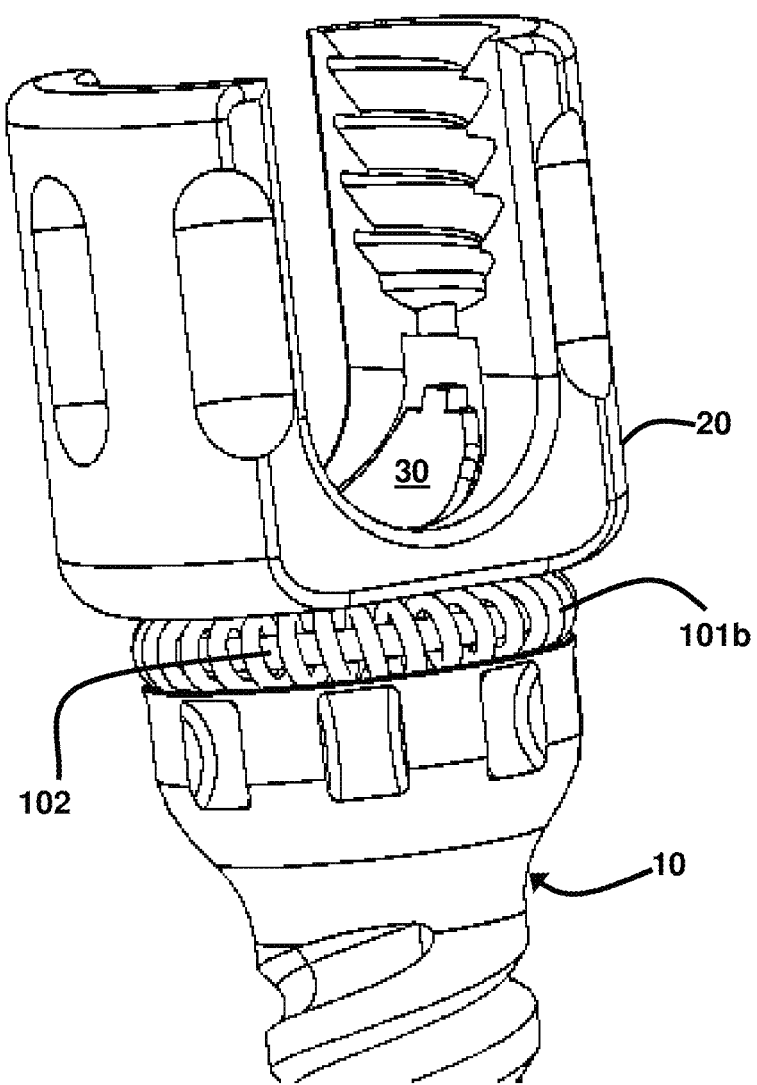
FIG. 8(A) is an isolated perspective view of the screw head and bone screw interface of FIG. 6(B) with an interior rounded washer according to the second embodiment herein.

FIGS. 6(A) and 7(A) illustrate an isolated view of the screw head and bone screw interface according to a first embodiment herein, wherein the load sharing mechanism 101 of FIGS. 1 through 5 is configured as a metallic wave/or hollowed washer 101a that could allow some structural collapse. FIGS. 6(B) and 7(B) illustrate an isolated view of the screw head and bone screw interface according to a second embodiment herein, wherein the load sharing mechanism 101 of FIGS. 1 through 5 is configured as a metallic coil spring 101b that is wrapped into a full diameter and may include an interior rounded washer 102 (as shown in FIGS. 8(A) and 8(B)) to further limit the range of motion.

Figure 6C:
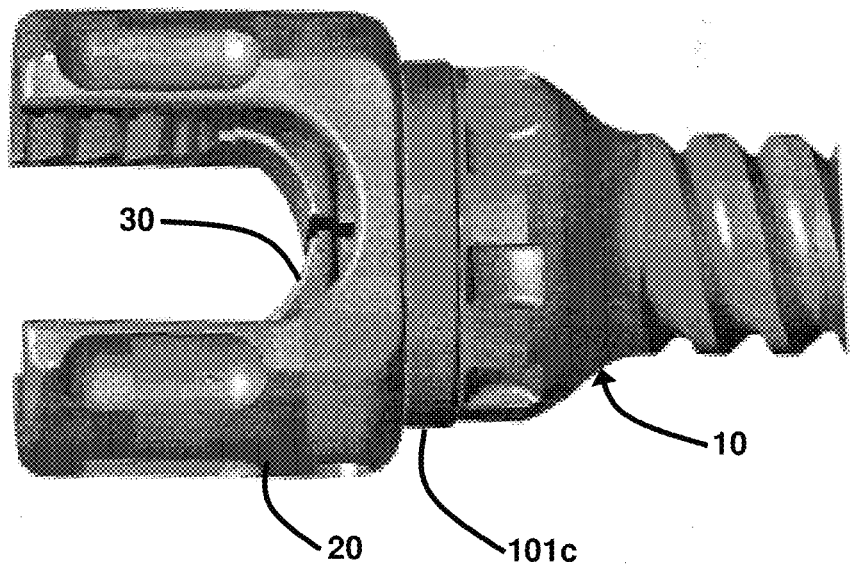
FIG. 6(C) illustrates an isolated perspective view of the screw head and bone screw interface according to a third embodiment herein.
Figure 6D:
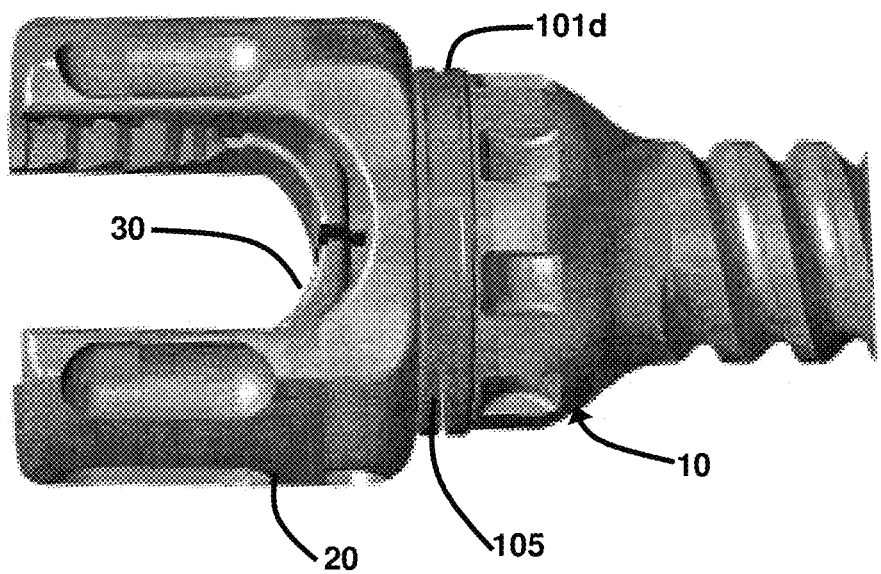
FIG. 6(D) illustrates an isolated perspective view of the screw head and bone screw interface according to a fourth embodiment herein.
Figure 7C:
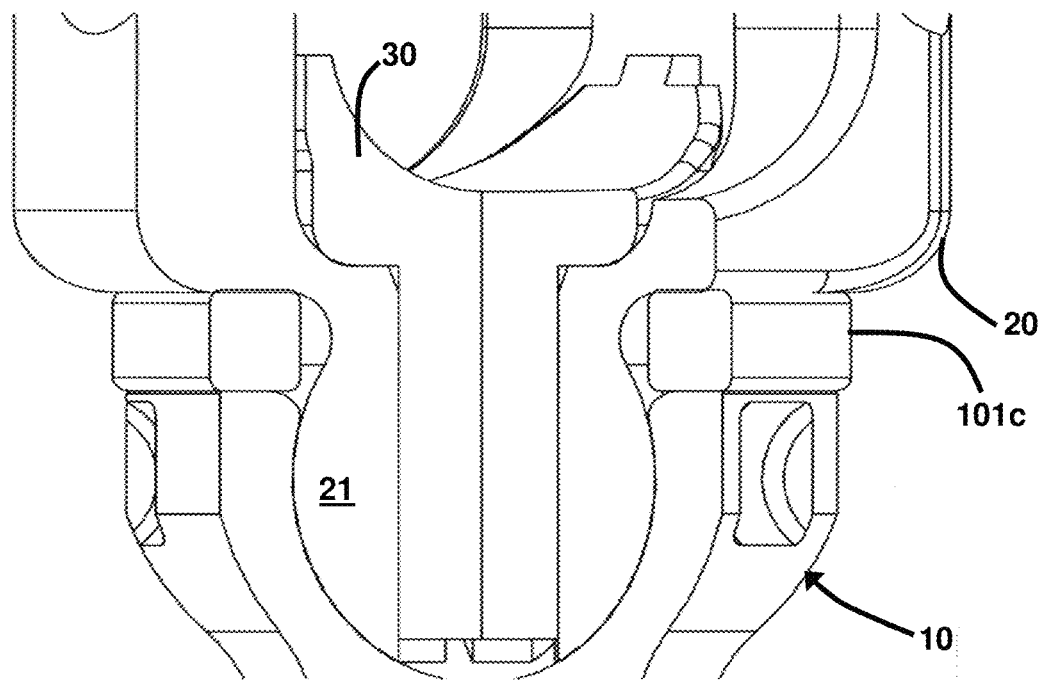
FIG. 7(C) is a cross-sectional view of the screw head and bone screw interface of FIG. 6(C) according to the third embodiment herein.
Figure 7D:
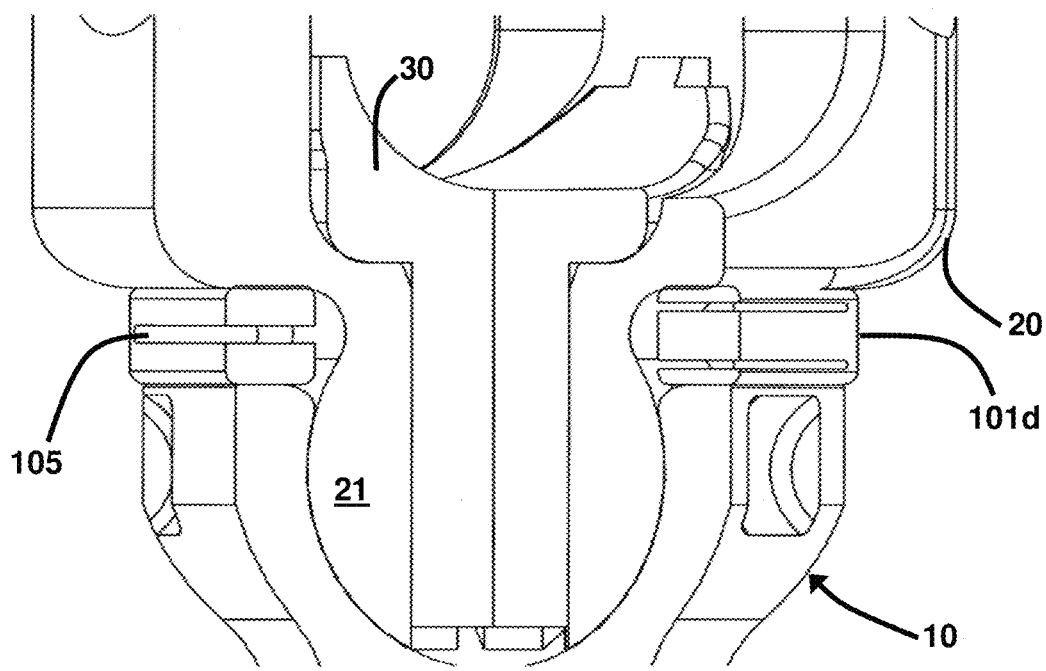
FIG. 7(D) is a cross-sectional view of the screw head and bone screw interface of FIG. 6(D) according to the fourth embodiment herein.

FIGS. 6(C) and 7(C) illustrate an isolated view of the screw head and bone screw interface according to a third embodiment herein, wherein the load sharing mechanism 101 of FIGS. 1 through 5 is configured as a flexible polymer washer 101c and may comprise silicon or urethane materials, for example. FIGS. 6(D) and 7(D) illustrate an isolated view of the screw head and bone screw interface according to a fourth embodiment herein, wherein the load sharing mechanism 101 of FIGS. 1 through 5 is configured as a metallic washer 101d with strategically placed cutouts 105 that can allow some structural collapse in desired locations or directions.

FIG. 9(A) illustrates the overall configuration of the screw head 20. FIG. 9(B) illustrates a front view of the screw head 20. FIG. 9(C) is a cross-sectional view from cut-line "CC" of FIG. 9(D). FIG. 9(E) is a cross-sectional view from cut-line "BB" of FIG. 9(F) and FIG. 9(G) is a cross-sectional view from cut-line "AA" of FIG. 9(F). Additionally, FIG. 9(H) is an enlarged detailed view of the encircled area "A" of FIG. 9(G) illustrating the threaded inner portion 23 in more detail. As shown in FIGS. 9(A) through 9(H), the screw head 20 includes a bulbous (spherical) male end 21 for engaging the concave female socket 12 of the bone screw. The screw head 20 also includes a pair of upright ends 22 opposite the bulbous male end 21, wherein the upright ends 22 comprise a threaded inner portion 23 for engaging the blocker 40. Furthermore, the screw head 20 includes a generally open U-shaped inner portion 24 for receiving the saddle pin 30 and the longitudinal member 50. The male end 21 of the screw head 20 includes a plurality (for example, four or more) slots 6 that allow the male end 21 to expand into the female spherical pocket 12 of the bone screw 10 at any allowable angle once the saddle pin 30 is forced through.

Since the screw head 20 is pivoting inside the female socket end 12 of the bone screw 10, the assembly 1 is allowed to be inserted deeper into the bone without having the bone or anatomy prematurely limit the range of angulations of the screw head 20. The screw head 20 further includes external features or cuts 29 that assist in accommodating surgical instrumentation during manipulation and assembly during the surgical procedure. These cuts 29 allow various instruments (not shown) to firmly and positively hold and manipulate the screw head 20 on one side or both sides of screw head 20.

Figure 10A:
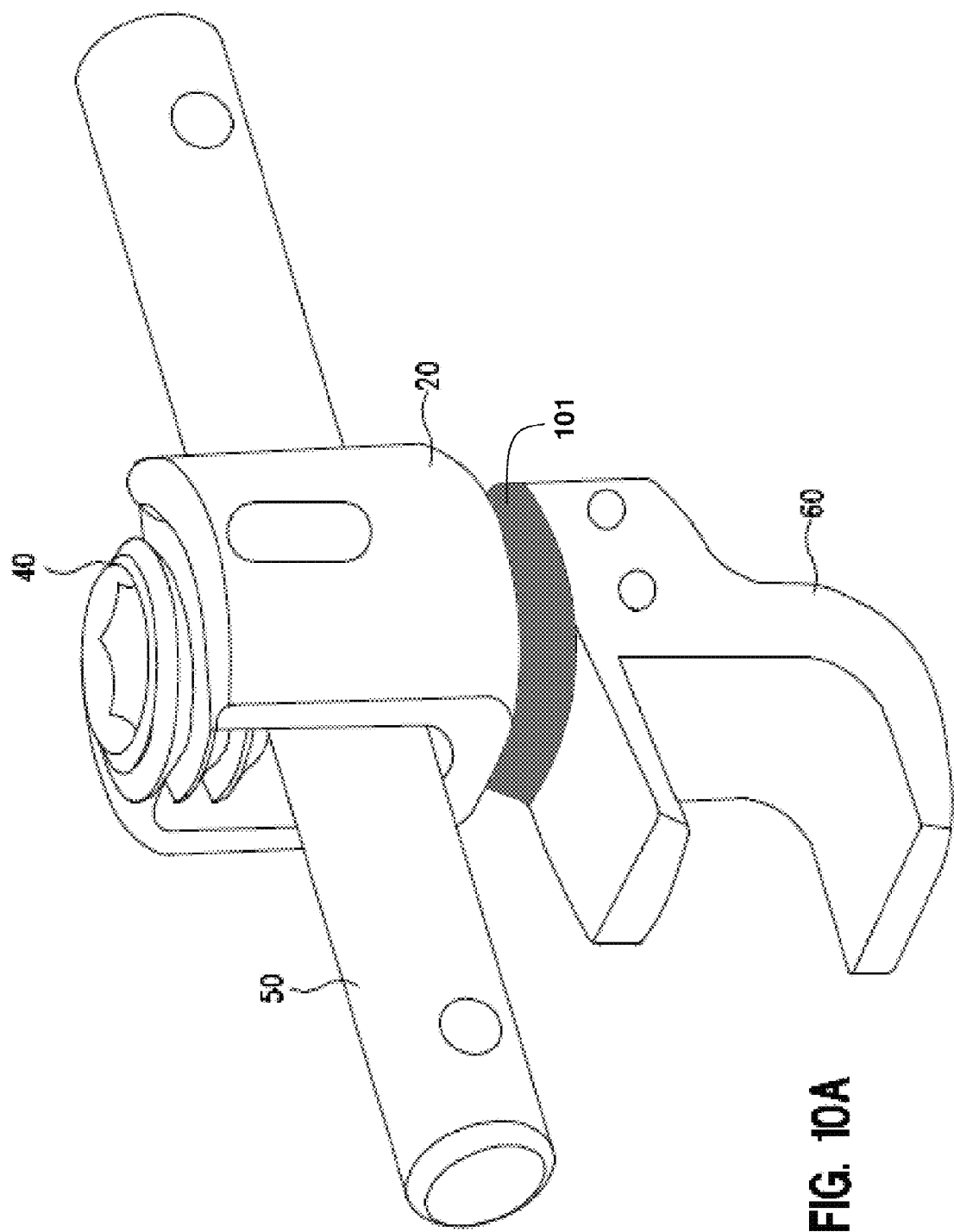
FIG. 10(A) is a perspective view of a bone fixator assembly according to an alternate embodiment herein.

FIG. 10(A) is a perspective view of a bone fixator assembly according to an alternate embodiment, wherein the bone fixator component is configured as a hook 60. The hook 60 is further illustrated in FIG. 10(B). The hook 60 includes a concave socket 12 having an inner portion 9 adapted to receive the bulbous end 21 of the screw head 20; and a dimpled outer portion 8. The hook 60 further includes a pair of arms 61, 62 connected by a connection arm 64. A space 63 separates the arms 61, 62 from one another. The arms 61, 62 are configured to receive an additional member (not shown) for subsequent attachment to the bone.

The several embodiments of the saddle pin 30 are shown in FIGS. 11(A) through 14. The saddle pin 30 provides a proper seat for the longitudinal member 50 and avoids notching a typical titanium longitudinal member 50 (titanium is very notch sensitive). Furthermore, the saddle pin 30 allows one to accommodate multiple sizes of longitudinal members 50 in the same screw assembly system 1 which is a first for a titanium system because of the above-mentioned notching factors. The saddle pin 30 is configured with a slot 32 through the center to allow expansion of the upper portion (head) 131 of the saddle pin 30. The bottom 35 of the saddle pin head 131 is angled to accommodate the saddle pin 30 when spreading to accept a larger-sized longitudinal member 50. The saddle pin 30 initially expands the male sphere 21 of the screw head 20 into the female spherical socket 12 in the bone screw 10 causing the screw assembly system 1 to lock or start locking (i.e., causing the male sphere 21 of the screw head 20 to lock in the female spherical socket 12 of the bone screw 10). The saddle pin 30 then "digs" into the female spherical socket 12 of the bone screw 10 to provide a secondary locking force to avoid bending failure of the assembly 1.

FIGS. 11(A) through 11(B) illustrate a first embodiment of the saddle pin 30. The saddle pin 30 generally includes an upper portion 131 and a lower portion 132. The upper portion includes as slot 32, which is configured from the lowest area 33 of the upper portion 131 into the upper area 34 of the lower portion 132 of the saddle pin 30. A secondary locking mechanism 36 may be configured on the lower portion 132 of the saddle pin to further achieve locking of the saddle pin 30 once it is inserted in the screw head 20. The lower portion 132 of the saddle pin 30 terminates with a pointed end 37 to allow for digging into the female socket 12 of the bone screw 10. FIGS. 12(A) through 12(B) illustrate a second embodiment of the saddle pin 30. The difference between the first and second embodiments of the saddle pin 30 is that the upper portion of the saddle pin 131 in the second embodiment includes two generally flat upper opposed ends 38 to more matingly configure with the geometry of the screw head 20 and the longitudinal member 50.

Figure 13:
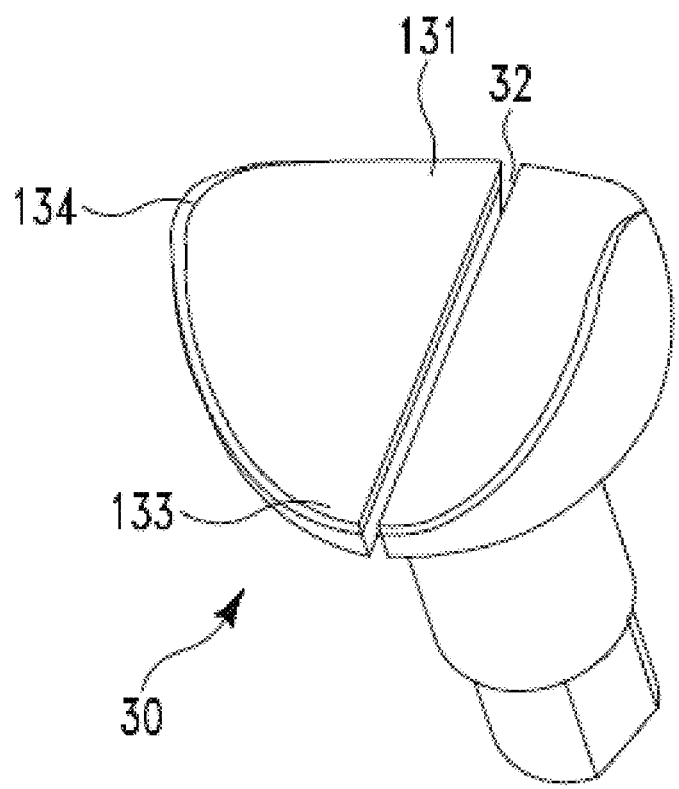
FIGS. 13 through 14 are detailed views of still alternate configurations of the saddle pin according to the embodiments herein.
Figure 14:
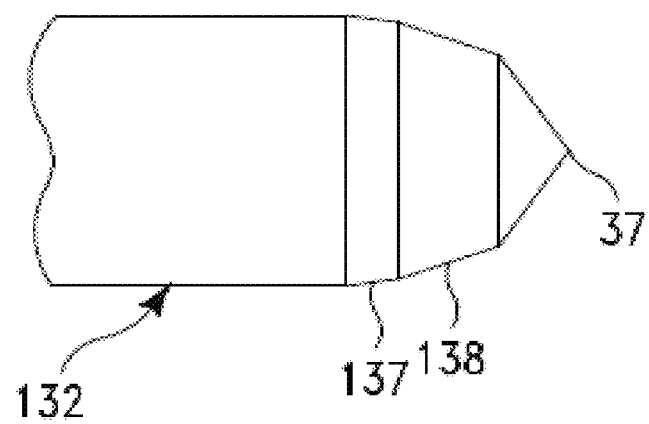

FIGS. 13 through 14 illustrate a third embodiment of the saddle pin 30. In particular, in the third embodiment, the saddle pin 30 comprises two parts: an upper portion 131 preferably comprising titanium and a lower portion 132 which is preferably ceramic. According to the third embodiment, the material of the lower portion 132 of the saddle pin 30 is preferably ceramic and has a higher hardness and compressive yield strength than the comparative hardness and compressive yield strength of $Ti_6Al_4V$, which is the material which may be used in constructing the screw head 20 and bone screw 10.

As shown in FIG. 13, the upper portion 131 of the saddle pin 30 includes a slot 32 in the seat portion 133 and tapered angled ends 134. Preferably, the saddle pin 30; i.e., the upper portion 131 and the ceramic tip 132 are assembled last in the overall process. Specifically, the screw head 20 snaps into the bone screw 10. Then, the ceramic tip 132 slides into the screw head 20, and finally the titanium saddle (upper portion) 131 is press fitted into the screw head 20 keeping everything in place and oriented in a relaxed state.

As best seen in FIG. 14, the lower portion 132 of the saddle pin terminates with a series of cascading walls 137, 138 having sloped angles, terminating with the pointed end 37 for attachment into the screw head 20/bone screw 10 assembly. The material properties of the saddle pin tip 134 are such that it prevents the deformation on the saddle pin 30 before the saddle pin 30 gives the proper bending and penetrating effects onto the screw head 20/bone screw 10 assembly. Examples of the types of materials used for the saddle pin pointed end 37 include Zyranox™ and HIP Vitox™, both of which are available from Morgan Advanced Ceramics, United Kingdom.

The blocker 40, which is further illustrated in FIGS. 15(A) through 15(C), includes a standard buttress thread 41 configured along an outer perimeter of the blocker 40. The blocker 40 helps to secure the longitudinal member 50 inside the screw head 40. The threads 41 of the blocker 40 are configured to engage the threads 23 of the screw head 20. Additionally, the blocker 40 aids in preventing the expansion of the screw head 20 when torqued on the longitudinal member 50, directing the counterforce more vertically than horizontally. The top 42 of the blocker 40 has a fastening feature 43 such as a hex or square lock feature to allow high torque to be applied in locking the assembly 1. Furthermore, the blocker 40 may be configured with a free rotating saddle (not shown) to accommodate, via tangential contact, the longitudinal member 50 and help to further prevent notching of the titanium alloy used to construct the longitudinal member 50. Moreover, the blocker 40 may have a "timed" thread 41 that is consistently and precisely related to the blocker driving tool (not shown) to help calculate the torsional and vertical position of the blocker 40 thereby assisting the torque measurement applied to the blocker 40.

Another aspect of the embodiments herein is illustrated in the flowchart of FIG. 16, which includes descriptions which refer to components provided in FIGS. 1 through 15(C). FIG. 8 illustrates a method of assembling a pedicle screw assembly 1, wherein the method comprises positioning (200) a load sharing mechanism 101, 101a, 101b, 101c, 101d in between a screw head 20 and a bone fixator component 10; attaching (210) the screw head 20 to the bone fixator component 10 such that the load sharing mechanism 101, 101a, 101b, 101c, 101d provides tensile resistance to said screw head 20; securing (220) the bone fixator component 10 in the bone (not shown); securing (230) a saddle pin 30 in the screw head 20; engaging (240) the saddle pin 30 with the bone fixator component 10; inserting (250) a longitudinal member 50 in the screw head 20; and inserting (260) a blocker 40 in the screw head 20. As mentioned, the embodiments herein provide an axial movement of the screw head up to 25 degrees in any plane. Moreover, the embodiments herein allow for greater medial translation of the longitudinal member 50 (nearly 4 mm compared to the conventional devices which are generally limited to 2 mm).

Moreover, according to an aspect of the embodiments herein, the assembly 1 can be used as a dynamic rod system to complement artificial discs. According to this embodiment, the outside of the spherical joint part 21 of the screw head 20 and the inner spherical surface of the bone screw cup 12 are coated with a wear resistant ceramic coating. In this scenario, the saddle pin 30 is not digging into the bone screw 10 and in fact is configured at a shorter length than some of the other embodiments. This system allows some motion instead of rigid fixation and shares the load with the artificial disc disallowing excessive forces being applied to the artificial disc and increasing its functional life. For example, this occurs as a result of the ceramic coating, which may be used in the embodiments herein. As such, the spherical joint 21 of the screw head 20 and the inner spherical surface 12 of the bone screw 10 have lower friction and higher wear resistance characteristics, thus improving the overall characteristics of the screw assembly 1.

Generally, as shown in FIG. 1 through 15(C), the embodiments herein provide an assembly 1 comprising a screw head 20 comprising a bulbous end 21; a fixator component 10 configured for receiving the bulbous end 21 of the screw head 20; a pin 30 mounted in the screw head 20; and a blocker 40 adapted to engage the screw head 20. The screw head 20 comprises a slot 24 configured for receiving a longitudinal member 50. The fixator component 10 comprises a concave socket 12 configured for receiving the bulbous end 21 of the screw head 20. In a first embodiment, the fixator component 10 also comprises a threaded end 11 opposite the concave socket 12 and configured for attaching to a bone. The pin 30 engages the fixator component 10 and a bottom portion 51 of the longitudinal member 50. The blocker 40 secures a top portion 52 of the longitudinal member 50. The pin 30 comprises an upper saddle portion 131 and a lower tip portion 132.

Additionally, the pin 30 may comprise a multi-part assembly. The upper saddle portion 131 of the pin 30 comprises titanium and the lower tip portion 132 of the pin 30 comprises a ceramic material. Moreover, the lower tip portion 132 comprises a mechanically harder material than the upper saddle portion 131. The screw head 20 and the fixator component 10 comprise a first material, and the lower tip portion 132 of the pin 30 comprises a material having a higher material hardness and compressive yield strength than the first material. The assembly 1 further comprises a wear resistant ceramic coating (not shown) over the screw head 20 and the fixator component 10.

Figure 10B:
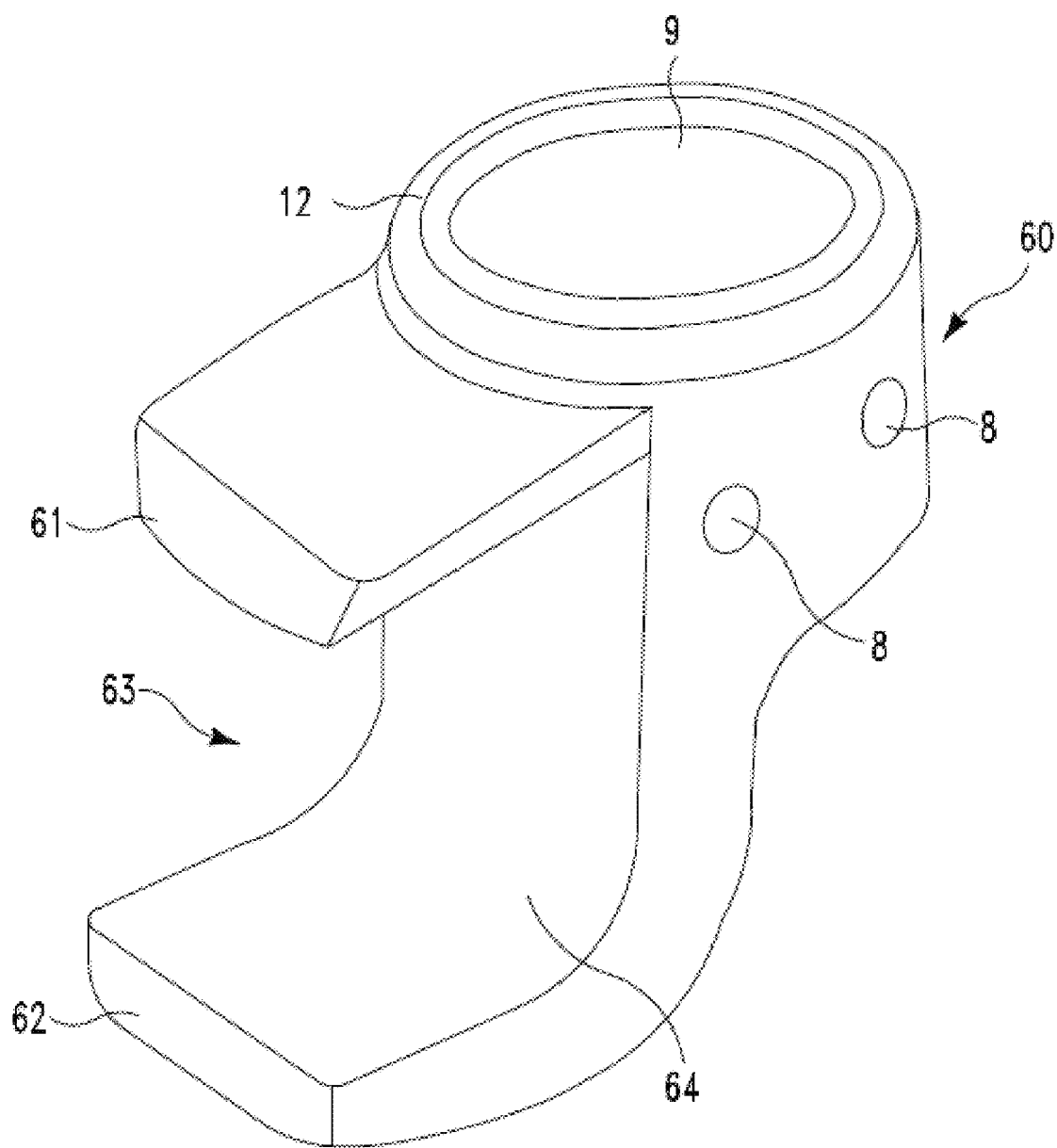
FIG. 10(B) is a detailed view of the hook of the bone fixator assembly of FIG. 10(A) according to the alternate embodiment herein.

The screw head 20 further comprises two opposed upright ends 22 separated by the slot 24, wherein each of the opposed upright ends 22 comprise an inner wall 27 and an outer wall 28, wherein the inner wall 27 comprises wall threads 23, and wherein the outer wall 28 comprises grooves (cuts) 29. The blocker 40 comprises blocker threads 41 configured around an outer perimeter 42 of the blocker 40, the blocker threads 41 being dimensioned and configured to mate with the wall threads 23. The upper saddle portion 131 of the pin 30 comprises a slot 32. The bulbous end 21 of the screw head 20 comprises a plurality of slots 6 terminating at an opening 4 at a tip 3 of the bulbous end 21. Moreover, the bulbous end 21 of the screw head 20 comprises a gap 19 configured to receive the pin 30. The concave socket 12 of the fixator component 10 comprises an inner portion 9 adapted to receive the bulbous end 21 of the screw head 20; and a dimpled outer portion 8. The fixator component 10 is configured as any of a threaded bone screw 10 (as shown in FIGS. 1 through 8) and a hook 60 (as shown in FIGS. 10(A) and 10(B)) according to the several embodiments herein.

The embodiments herein provide a pedicle screw assembly implant device 1 that has a load sharing mechanism 101 adapted to allow the screw head 20 to have an increased tensile load, and such that the assembly 1 may be used anteriorly or posteriorly, and which is capable of being utilized in surgeries to achieve anterior lumbar interbody fusion, posterior lumbar interbody fusion, transverse lumbar interbody fusion, correct degenerative disc disease, adult and pediatric scoliosis as a fixation device, and posterior cervical fusion.

The embodiments herein also offer the surgeon more lateral range of motion than conventional products by utilizing the space under the screw head to provide a bigger arc of rotation. Moreover, the saddle pin 30 component offers the flexibility to use a diametrical range of spinal longitudinal members 50 instead of a fixed size longitudinal member.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A method of assembling a pedicle fixation assembly, wherein said method comprises: positioning a load sharing mechanism in between a screw head and a bone fixator component; configuring said fixator component with a concave socket that is configured for receiving an expandable bulbous end of said screw head, wherein said bulbous end comprising a plurality of flanges; attaching said screw head to said bone fixator component such that said load sharing mechanism provides tensile resistance to said screw head; securing said bone fixator component in a bone; securing a locking pin in said screw head; engaging said locking pin with said bone fixator component; inserting a longitudinal member in said screw head; and inserting a blocker in said screw head.

2. The method of claim 1, further comprising positioning a longitudinal member in a slot configured in said screw head.

3. The method of claim 1, further comprising configuring said load sharing mechanism as any of a wave washer, a collapsible hollow washer, a coiled spring, and a flexible washer.

4. The method of claim 1, further comprising configuring said load sharing mechanism as a washer having an outer surface with a plurality of cutout portions configured therein.

5. The method of claim 1, further comprising configuring said fixator component as a bone screw.

6. The method of claim 1, further comprising configuring said fixator component as a hook.

7. A method comprising:
connecting a bone fixator component to a vertebral body, wherein said bone fixator component comprises an open concave head;
providing a screw head comprising:
a bulbous body comprising a plurality of outwardly expandable legs adapted to lock into said open concave head of said bone fixator component, wherein said bulbous body comprises a dynamic diameter and said dynamic diameter is between a first diameter and a second diameter; and
an upper portion permanently coupled to said bulbous body and comprising a fixed width, wherein said fixed width is greater than said first diameter;
positioning a load sharing mechanism in between said bone fixator component and said screw head, said load sharing mechanism comprising:
an inner load sharing mechanism diameter; and
an outer load sharing mechanism diameter, wherein said inner load sharing mechanism diameter is less than said outer load sharing mechanism diameter, mounting a pin in said screw head causing expansion of said bulbous body from said first diameter to said second diameter; and engaging a blocker with said screw head.

8. The method of claim 7, wherein said load sharing mechanism comprises any of a wave washer, a collapsible hollow washer, and a flexible washer.

9. The method of claim 7, wherein said load sharing mechanism comprises a spring mechanism comprising a coiled spring wrapped in a first spring diameter and an interior rounded washer within said coiled spring.

10. The method of claim 7, wherein said load sharing mechanism comprises a washer comprising:
   a top surface;
   a bottom surface; and
   a side surface with a plurality of cutout portions configured therein,
   wherein said plurality of cutout portions are parallel to said top surface and said bottom surface.

11. The method of claim 7, wherein said load sharing mechanism comprises a flexible polymer washer.

12. The method of claim 7, wherein said screw head further comprises:
   a slot adapted to receive a longitudinal member; and
   a plurality of opposed upright ends separated by said slot, wherein each of said opposed upright ends comprise an inner wall and an outer wall, wherein any of said inner wall and said outer wall comprises wall threads, and wherein any of said inner wall and said outer wall comprises grooves.

13. The method of claim 12, wherein said bulbous body further comprises a plurality of flanges and an inner portion, wherein said inner portion comprises a channel bored through said bulbous body, and wherein said pin is mounted within an inner portion of said screw head causing outward expansion of said legs of said bulbous body.

14. A method comprising:
providing a screw head comprising:
   an outwardly protruding and expandable bulbous end comprising a plurality of flanges and an inner portion, wherein said inner portion comprises a channel bored through said bulbous end;
   a slot adapted to receive a longitudinal member; and
   a pair of opposed upright ends separated by said slot, wherein each of the opposed upright ends comprises an inner wall and an outer wall, wherein said inner wall comprises wall threads, and wherein said outer wall comprises grooves;
configuring a fixator component to receive the bulbous end of said screw head;
positioning a load sharing mechanism in between said bulbous end of said screw head and said fixator component, wherein said load sharing mechanism provides tensile resistance to said screw head;
mounting a pin within an inner portion of said screw head causing said flanges of said bulbous end to expand, wherein said pin sits in said channel; and
engaging a blocker with said screw head, wherein said blocker comprises blocker threads that mate with said wall threads.

15. The method of claim 14, wherein said screw head comprises an open "U" shaped inner portion comprising said slot and said plurality of opposed upright ends.

16. The method of claim 14, wherein said fixator component comprises a concave socket configured for receiving said bulbous end of said screw head.

17. The method of claim 14, wherein said load sharing mechanism comprises any of a wave washer, a collapsible hollow washer, a coiled spring, and a flexible washer.

18. The method of claim 14, wherein said load sharing mechanism comprises a washer having an outer surface with a plurality of cutout portions configured therein.

19. The method of claim 14, wherein said fixator component comprises any of a bone screw and a hook.

* * * * *